(12) United States Patent
Kato

(10) Patent No.: US 11,725,182 B2
(45) Date of Patent: Aug. 15, 2023

(54) ALGAE-BASED BIOPLASTICS AND METHODS OF MAKING

(71) Applicant: Board of Supervisors of Louisiana State University and Agricultural and Mechanical College, Baton Rouge, LA (US)

(72) Inventor: Naohiro Kato, Baton Rouge, LA (US)

(73) Assignee: Board of Supervisors of Louisiana State University, Baton Rouge, LA (US)

( * ) Notice: Subject to any disclaimer, the term of this patent is extended or adjusted under 35 U.S.C. 154(b) by 499 days.

(21) Appl. No.: 16/753,877

(22) PCT Filed: Oct. 9, 2018

(86) PCT No.: PCT/US2018/054928
§ 371 (c)(1),
(2) Date: Apr. 6, 2020

(87) PCT Pub. No.: WO2019/074876
PCT Pub. Date: Apr. 18, 2019

(65) Prior Publication Data
US 2020/0263125 A1 Aug. 20, 2020

Related U.S. Application Data

(60) Provisional application No. 62/569,871, filed on Oct. 9, 2017.

(51) Int. Cl.
| | |
|---|---|
| *C12N 1/12* | (2006.01) |
| *C12P 7/6463* | (2022.01) |
| *C08H 99/00* | (2010.01) |
| *C08L 99/00* | (2006.01) |
| *A01G 33/00* | (2006.01) |

(52) U.S. Cl.
CPC ............. *C12N 1/12* (2013.01); *A01G 33/00* (2013.01); *C08H 99/00* (2013.01); *C08L 99/00* (2013.01); *C12P 7/6463* (2013.01)

(58) Field of Classification Search
None
See application file for complete search history.

(56) References Cited

U.S. PATENT DOCUMENTS

| | | |
|---|---|---|
| 8,026,301 B2 | 9/2011 | Sumanam |
| 8,526,811 B2 | 9/2013 | Xie et al. |
| 2013/0220173 A1 | 8/2013 | Sharma et al. |
| 2013/0236937 A1* | 9/2013 | Harlin .................. C12P 7/6445 502/402 |
| 2014/0134685 A1* | 5/2014 | Benning ............ C12N 15/8247 435/252.33 |
| 2017/0009197 A1 | 1/2017 | Harlin et al. |
| 2017/0073711 A1 | 3/2017 | Iwai et al. |

OTHER PUBLICATIONS

Yao et al. "Microalgae Lipid Characterization", Journal of Agricultural and Food Chemistry, vol. 63, pp. 1773-1787 (Year: 2015).*
International Search Report for International Application No. PCT/US2018/054928, dated Jan. 28, 2019.

* cited by examiner

*Primary Examiner* — Michelle F. Paguio Frising
(74) *Attorney, Agent, or Firm* — Thomas|Horstemeyer, LLP

(57) ABSTRACT

Provided for are methods of producing triacylglycerol-accumulated microalgae, methods for making bioplastics from triacylglycerol-accumulated microalgae, methods for making alga-mixed plastics, and products including these bioplastics. Methods of triacylglycerol accumulation using centrifugation are also provided. Products such as plastic beads and other consumer products can be made from the bioplastics described herein.

10 Claims, 14 Drawing Sheets

Algaculture systems and a molding machine
in NAP LLC / in Noble Plastics LLC

ALGAE-BASED BIOPLASTICS AND METHODS OF MAKING

CROSS-REFERENCE TO RELATED APPLICATIONS

This application is the 35 U.S.C. § 371 national stage of PCT application having serial number PCT/US2018/054928, filed on Oct. 9, 2018. This application also claims the benefit of and priority to U.S. Provisional Application Ser. No. 62/569,871, having the title "ALGAE-BASED BIOPLASTICS AND METHODS OF MAKING", filed on Oct. 9, 2017, the disclosure of which is incorporated herein by reference in its entirety.

BACKGROUND

The demand for biologically produced and degradable plastics, bioplastics, has increased in recent years due to increasing public concern about the environment, climate change, and limited fossil fuel resources. Although the raw materials for bioplastics, biopolymers, are commercially produced, these biopolymers are not competitive against petroleum-based polymers economically due to their high cost of production and purification. As the result, the use of bioplastics in the market is limited. An example of the limitation can be found in Mardi Gras beads, those plastic necklaces thrown during the annual Carnival celebration in Louisiana and elsewhere. It is a tradition in Louisiana that riders of Mardi Gras parades (krewes) throw the beads to people in the streets. Although Mardi Gras beads are historically made of glass, recent Mardi Gras beads are made of petroleum-based polyethylene or polystyrene, known as mold-on-thread (MOT) beads in the industry. An analysis estimates that about 11 million tons of plastic ornaments, including MOT, are imported to New Orleans, the largest city in Louisiana, each year for the celebration, but many of them end up in landfills. Local organizations encourage recycling the beads and throwing eco-friendly beads (i.e., paper beads) to conserve resources while preserving the tradition. However, the impact of the efforts has been limited. Because people in the streets seek krewes to throw many beads and the budgets of the krewes are limited, so inexpensive Mardi Gras beads are widely used.

Mardi Gras beads are a big industry in Louisiana with over 25 million pounds of beads imported each year, bringing in about $12 million in sales annually. Mardi Gras beads contribute to the roughly 150 tons of waste produced from Mardi Gras each year. Beads pose environmental and health hazards since they contain lead. The majority of lead in the soil found in various parts of New Orleans was discovered to be located directly alongside the Mardi Gras parade routes, which translates to about 4,000 pounds of lead hitting the streets. The demand for affordable, biologically produced and degradable Mari Gras beads, such as bioplastic Mardi Gras beads, has increased in recent years due to increasing public concern about the environment, health, and limited fossil fuel resources. An example is that of Zombeads, a private company, which has created beads with recycled paper.

Various methods of manufacturing Mardi Gras beads have been investigated in the past. From the 1970s until now, there have been about 50 styles of machine-styled beads, including plastic and polystone medallions beads, and current trends such as lighted beads. Generally speaking, the bead making process takes 90 to 100 days and is very labor intensive. First, a plastic mold is manufactured. During the machine-tooled process, plastic is injected into the mold, forming the bead. From there, it is sent to the metallizer, where color is added. An employee then pulls the bead string out, which can be as long as half a mile, and cuts it to the appropriate size. In the next step, the two ends of the bead are fused together and any extra items, such as a medallion, are added. The beads are then hand-stapled into groups and bagged. From there, they are loaded into containers and shipped to the United States, with shipping taking 21 to 24 days.

BRIEF DESCRIPTION OF THE DRAWINGS

Further aspects of the present disclosure will be more readily appreciated upon review of the detailed description of its various embodiments, described below, when taken in conjunction with the accompanying drawings.

DETAILED DESCRIPTION

Figure 1:
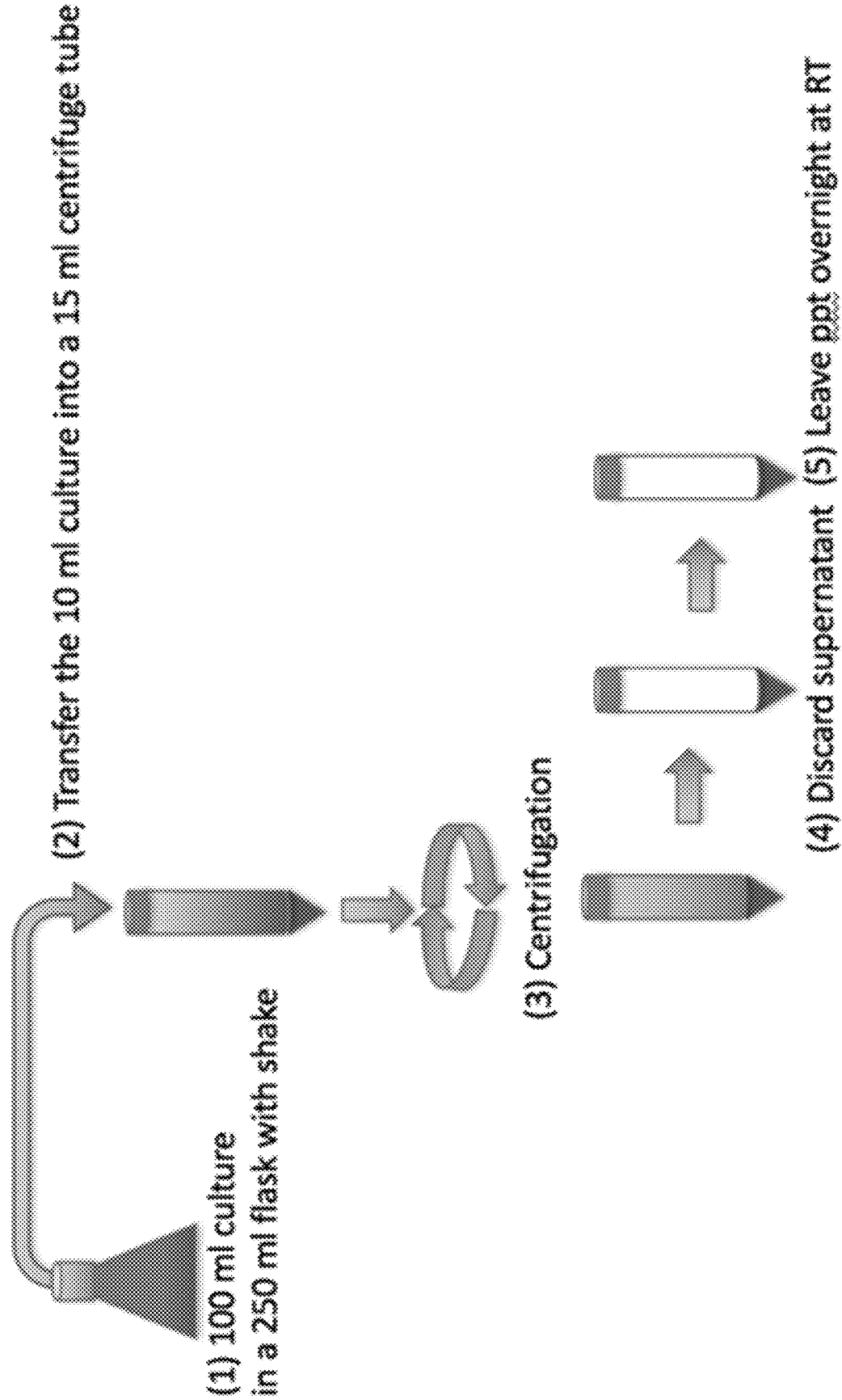
FIG. 1 illustrates an embodiment of a method for the centrifugation-induced triacylglycerol production.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range.

Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents that are specifically incorporated by reference herein, are incorporated by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, microbiology, material science, and the like, which are within the skill of the art.

The following examples are put forth so as to provide those of ordinary skill in the art with a complete disclosure and description of how to perform the methods and use the materials disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

Definitions

As used herein, "triacylglycerol-accumulated *Chlamydomonas*" refers to *Chlamydomonas* that has been modified to produce increased triacylglycerol (TAG) through stress conditions, e.g. through centrifugation, nitrogen depletion, iron deficiency, high salinity, high temperature and the like. A triacylglycerol-accumulating microalgae (such as, but not limited to a triacylglycerol-accumulating *Chlamydomonas*) is a species of microalgae that will produce increased triacylglycerol (TAG) through stress conditions, as compared to the amount of TAG produced by the species of microalgae in normal (e.g., non-stress) conditions.

General Discussion

In accordance with the purpose(s) of the present disclosure, as embodied and broadly described herein, embodiments of the present disclosure, in some aspects, relate to bioplastics made from triacylglycerol-accumulated microalgae, methods for making triacylglycerol-accumulated microalgae, methods for making bioplastics from triacylglycerol-accumulated microalgae, methods for making alga-mixed plastics, and products including these bioplastics. As discussed above, the accumulation of plastics, such as the millions of pounds of Mardi Gras Beads produced each year, poses a plethora of environmental problems. Biodegradable plastics offer a possible alternative, but such plastics are not yet widespread due to cost of production and various drawbacks.

Biologically produced and degradable plastics can be based on bio-compounds such as starch, cellulose, protein, aliphatic polyesters. Triacylglycerol (TAG) is an esterified molecule derived from a glycerol and three fatty acids and can also provide a raw material for the production of bioplastics [7, 8]. Studies in chemical engineering show that TAG can be plasticized by crosslinking the molecule through the coupling of the free radicals that are formed from the decomposition of hydroperoxide. These bio-compounds are typically extracted and purified from plants or bacteria.

Algae offers an avenue for bioplastic production due to their high biomass yield, ability to be cultivated in a natural environment, reduced production cost and reduced impact on the food chain, unlike with plant-based bioplastics [34, 35]. It is technically feasible to incorporate dried algae refined to a small particle size (<150 μm) and added whole to thermoplastic blend formulations [36]. Various compositions of different algae species have been investigated for use as a bioplastic or thermoplastic as each species have different properties that may impact their effectiveness as a bioplastic. The enormous diversity in the algal lineages is due to their long evolutionary history. As a result, microalgae exhibit wide variation in both cellular architecture and biosynthetic capacity, and thus present the potential for a broad array of applications [37]. Adding synthetic polymers such as polyethylene to bioplastic compositions have also been investigated as an avenue to improve mechanical performance.

Zeller et al. [38], investigated bioplastics and thermoplastic blends made solely from *Spirulina* and *Chlorella* microalgae and the influence of blending with polyethylene on mechanical performance of *Spirulina* and *Chlorella* based thermoplastic blends.

Wang et al. (2016) investigated the protein modification of catfish algae (planktonic algae) and *Nannochloropsis* (microalgae) and also investigated the influence of various factors such as types of algae, scavenger materials (adsorbents), synthetic resin, and compatibilizer on the odor of plastics.

U.S. Pat. No. 8,524,811 (herein incorporated by reference) discloses a thermoplastic composition comprising *Nannochloropsis, Spirulina, Chlorella*, or a combination thereof mixed with a plant polymer. The disclosure teaches melting a microalgae powder composition consisting of *Nannochloropsis, Spirulina, Chlorella*, or a combination thereof; a plasticizer, and a plant polymer and extruding at about 80 Celsius degree to 190 Celsius degree under conditions of melt pressure 5-20 bar and torque 40-80%.

Additionally, various methods of producing algae based bioplastics or thermoplastics have been investigated. Wang [36] teaches the preparation of algae bioplastic composed of catfish algae (planktonic algae) and *Nannochloropsis* (microalgae) through thermomechanical compression molding using a benchtop press with electrically heated and water-cooled platens for a 20 min. cook time at +/−150° C., followed by 10 min. cooling period, and both performed under pressure greater than 24,000 Pa.

TAG production in microalgae has been also studied for industrial use because microalgae are capable of producing TAG efficiently [9]. Among the microalgae, *Chlamydomonas reinhardtii* has been studied as a model organism [10]. The studies on *Chlamydomonas* found that it produces TAG when it is in stress environments, such as nitrogen depletion [11], iron deficiency [12], high salinity [11], and high temperature [13].

Nevertheless, many challenges remain in the art before algae based bioplastics can be produced at commercially viable scale due to a high cost of the production and purification [37]. One of the solutions to reduce the production cost of the bioplastics is to mold crude bioplastics, a whole biomass accumulating the biopolymers, A study shows that a biomass of bacteria accumulating PHA (polyhydroxyalkanoate), the aliphatic polyester, can be molded without the extraction and purification of PHA [6].

Due to a lack of economic competitiveness of biologically produced polymers against the petroleum-based polymers, the Mardi Gras beads made of biopolymers are not yet commercially available, even if locals favor the conservation of resources. One of the solutions to reduce the production cost of the bioplastics is to mold crude bioplastics via a whole biomass accumulating the biopolymers without the need for extraction and purification. A study [6] shows that a biomass of bacteria accumulating polyhydroxyalkanoate (PHA), the biopolymer, can be molded without the extraction and purification of PHA.

Triacylglycerol (TAG) is an esterified molecule derived from a glycerol and three fatty acids and can be a raw material for the bioplastics. The studies in chemical engineering show that TAG can be plasticized by crosslinking the molecule through the coupling of the free radicals that are formed from the decomposition of hydroperoxide. TAG production in microalgae has been widely studied for industrial use because microalgae are capable of producing TAG efficiently [9]. Among the microalgae, *Chlamydomonas reinhardtii* has been studied as a model organism. The studies on *Chlamydomonas* found that it produces TAG when it is in stressful environments, such as nitrogen depletion, iron deficiency, high salinity, and high temperature. The present disclosure demonstrates that microalgae accumulating TAG will be an economically sustainable crude bioplastic because they can produce not only bioplastic materials but also commercially valuable carotenoids, By sequentially producing carotenoids and crude-bioplastics from the same microalgal culture, a cost of the bioplastic production can be reduced.

In general, embodiments of the present disclosure provide for methods of producing triacylglycerol-accumulated microalgae, methods for making bioplastics from triacylglycerol-accumulated microalgae, methods for making alga-mixed plastics, and products including these bioplastics.

The present disclosure includes a bioplastic mass including triacylglycerol-accumulated *Chlamydomonas*. Advantageously, the bioplastic mass is renewable and biodegradable, with low production costs, low impact on the food chain, and high yield.

Embodiments of the present disclosure include a bioplastic mass as above, wherein the bioplastic mass does not contain thermoplastics. The bioplastic mass can be an algae biomass molded without other thermoplastic materials.

Embodiments of the present disclosure include a bioplastic mass as above, wherein the triacylglycerol-accumulated *Chlamydomonas* is crosslinked.

Embodiments of the present disclosure include a bioplastic mass as above, further comprising *Chlorella*, wherein the triacylglycerol-accumulated *Chlamydomonas* is crosslinked with the *Chlorella*.

Embodiments of the present disclosure include a bioplastic mass as above, wherein the crosslinking is performed under heated conditions of about 120° C.

Embodiments of the present disclosure include a bioplastic mass as above, further including at least one additive to strengthen the bioplastic. In embodiments, the additive is an oxidizer (such as, but not limited to ammonium persulfate, hydrogen peroxide, Sodium persulfate). In other embodiments, the additive is a plasticizer (such as, but not limited to polyethylene, glycerol).

Embodiments of the present disclosure include a bioplastic mass as above, wherein the triacylglycerol-accumulated *Chlamydomonas* is produced by centrifugation.

The present disclosure includes methods for making bioplastics including culturing one or more genus of microalgae, wherein at least one of the genera is a triacylglycerol-accumulating microalgae; centrifuging the microalgae during the stationary phase to induce polymer compound accumulation; extracting precipitate (also referred to as biomass or algal biomass) formed during centrifugation; incubating and dehydrating the precipitate; grinding the precipitate to form a powder and mixing with water to form a mixture; and adding at least one additive to form the bioplastic, wherein the additive is selected from an oxidizer, a plasticizer, and a combination thereof.

Embodiments of the present disclosure include a method as above, wherein the triacylglycerol-accumulating microalgae includes *Chlamydomonas*. In other embodiments, the microalgae can include diatom species, *Nannochloris*, and *Botryococcus*.

Embodiments of the present disclosure include a method as above, wherein the microalgae further comprises *Chlorella*.

Embodiments of the present disclosure include a method as above, wherein when the microalgae is *Chlamydomonas reinhardtii*, the accumulated polymer is triacylglycerol, and when the microalgae is *Chlorella vulgaris*, the accumulated polymer is selected from starch, triglyceride, cellulose, proteins, and a combination thereof.

Embodiments of the present disclosure include a method as above, wherein the additive is selected from ammonium persulfate, glycerol, and a combination thereof.

Embodiments of the present disclosure include a method as above, wherein the additive is from about 5% w/dw to about 15% w/dw, or about 10% w/dw of the biomass (e.g. the precipitate).

Figure 9:
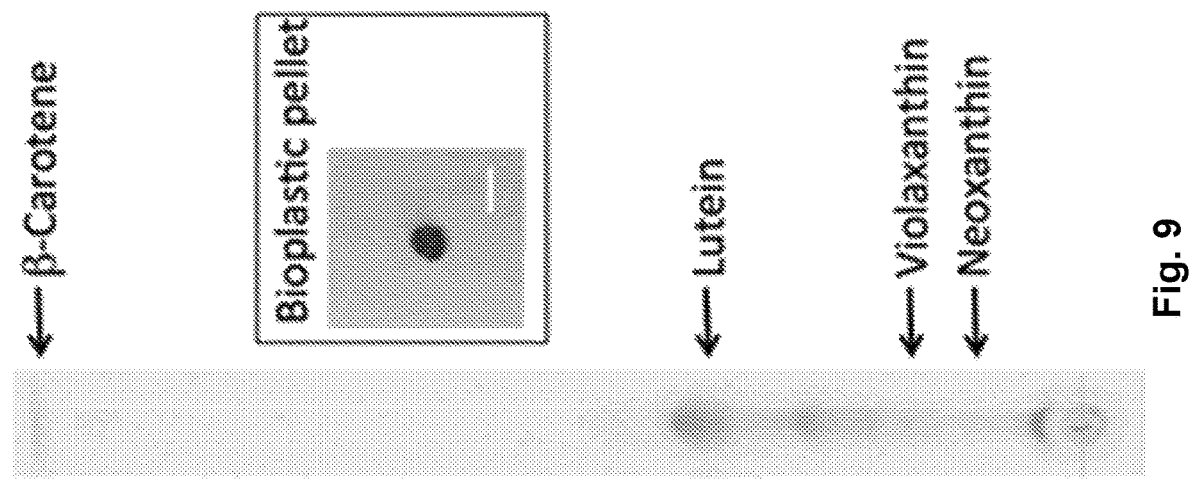
FIG. 9 illustrates the production of algaplastic without negative effect after carotenoids have been eluted.

Embodiments of the present disclosure include a method as above, wherein the method further comprises eluting carotenoids from supernatant generated during the centrifugation. Advantageously, the method sequentially produces carotenoids, commercially valuable bioactive-compounds, and bioplastics from the same microalgal culture. The carotenoids can be isolated from an algae, and the leftover algae biomass molded into a bioplastic without mixing thermoplastics (see FIG. 9). It is also possible to mix the leftover algae biomass into thermoplastics (see FIGS. 10A-D, 11).

The present disclosure includes a method for making bioplastics including culturing one or more genus of microalgae, wherein at least one of the genera is a triacylglycerol-accumulating microalgae; centrifuging the microalgae during the stationary phase to induce polymer compound accumulation; extracting precipitate formed during centrifugation; incubating and dehydrating the precipitate; grinding the precipitate to form a powder and mixing with water to form a mixture; adding at least one additive to the mixture to form the bioplastic, wherein the additive can be an oxidizer, a plasticizer, or a combination thereof; heating the mixture to about 120° C.; and molding the mixture into a shape.

Embodiments of the present disclosure include a method as above, wherein the microalgae comprises *Chlamydomonas* and optionally includes *Chlorella*.

Embodiments of the present disclosure include a method as above, wherein when the microalgae is *Chlamydomonas reinhardtii*, the accumulated polymer is triacylglycerol, and when the microalgae is *Chlorella vulgaris*, the accumulated polymer is selected from starch, triglyceride; cellulose, proteins, and a combination thereof.

Embodiments of the present disclosure include a method as above, wherein the additive is selected from ammonium persulfate, glycerol, and a combination thereof.

Embodiments of the present disclosure include a method as above, wherein the additive is from about 5% w/dw to about 15% w/dw of the biomass.

Embodiments of the present disclosure include a method as above, wherein the method further comprises eluting carotenoids from supernatant generated during the centrifugation. Advantageously, the method sequentially produces carotenoids, commercially valuable bioactive-compounds, and bioplastics from the same microalgal culture.

The present disclosure includes a bioplastic mass formed by the steps of: culturing one or more genus of microalgae; wherein at least one of the genera is a triacylglycerol-accumulating microalgae; centrifuging the microalgae during the stationary phase to induce polymer compound accumulation; extracting compounds from precipitate formed during centrifugation; incubating and dehydrating the precipitate; grinding the precipitate to form a powder and mixing with water to form a mixture; and adding at least one additive to form the bioplastic, wherein the additive is selected from an oxidizer, a plasticizer, and a combination thereof.

Embodiments of the present disclosure include a method as above, further formed by the additional steps of: heating the mixture to about 120° C.; and molding the mixture into a shape.

Embodiments of the present disclosure include a method as above, wherein the microalgae comprises *Chlamydomonas* and optionally includes *Chlorella*.

Embodiments of the present disclosure include a method as above, wherein when the microalgae is *Chlamydomonas reinhardtii*, the accumulated polymer is triacylglycerol, and when the microalgae is *Chlorella vulgaris*, the accumulated polymer is selected from starch, triglyceride, cellulose, proteins, and a combination thereof.

Embodiments of the present disclosure include a method as above, wherein the additive is selected from ammonium persulfate, glycerol, and a combination thereof.

Embodiments of the present disclosure include a method as above, wherein the additive is from about 5% w/dw to about 15% w/dw of the biomass.

The present disclosure includes an algae mixed plastic comprising triacylglycerol-accumulated microalgae and polyethylene.

Embodiments of the present disclosure include a method as above, wherein the triacylglycerol-accumulated microalgae is *Chlamydomonas*.

Embodiments of the present disclosure include a method as above, further comprising *Chlorella*.

Embodiments of the present disclosure include a method as above, further comprising an additive selected from ammonium persulfate, glycerol, and a combination thereof.

Embodiments of the present disclosure include a method as above, wherein the triacylglycerol-accumulated *Chlamydomonas* is produced by centrifugation.

Embodiments of the present disclosure include a method as above, comprising: selecting and culturing a species of microalgae capable of triacylglycerol accumulation from centrifugation; centrifuging the cultured microalgae during the stationary phase of growth; extracting compounds from precipitate formed during centrifugation; and incubating the precipitate, resulting in triacylglycerol-accumulated microalgae.

Embodiments of the present disclosure include a method as above, wherein the cultured species of microalgae is from the genus *Chlamydomonas*.

Embodiments of the present disclosure include a method as above, wherein the amount of triacylglycerol accumulated in the microalgae after incubation is from about 200% to about 400% higher than triacylglycerol accumulation produced by microalgae subjected to stress conditions other than centrifugation.

Embodiments of the present disclosure include a method as above, wherein the microalgae contains less C18 fatty acid methyl esters than in a comparable sample produced by nitrogen depletion.

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

EXAMPLES

The demand for bioplastics has increased in recent years, yet their application in industries has been limited. One of the reasons is the high cost of producing and purifying biopolymers, the raw materials for the bioplastics. The present disclosure demonstrates that *Chlamydomonas reinhardtii*, a model microalga, produces increased amounts of the biopolymer triacylglycerol (TAG) when the cells are left overnight after centrifugation. The centrifuged cells produce triacylglycerol about 3-fold higher than those cultured in a nitrogen depletion condition in the first 24 hours. The chloroplast membranes of the centrifuged cells are largely disrupted. In addition, the accumulated triacylglycerol rarely contains C18:1 (11) and C18:3 (5,9,12) fatty acids that are normally found in triacylglycerol in the cells cultured in the nitrogen depletion condition. Advantageously, different triacylglycerols can be produced using the centrifugation methods described herein than can be produced using nitrogen depletion without genetic modification. These suggest that the centrifuged cells produce triacylglycerol differently from those cultured in the nitrogen depletion condition. It was also found that the centrifuged cells, the biomass, can be molded to a bead that cracks at 1.7 MPa. The methods developed in this study provide methods to produce economically viable disposable-bioplastics.

During a time-course experiment, when the centrifuged biomass was accidentally left on a laboratory bench overnight, it was unexpectedly found that *Chlamydomonas* produces TAG. During the characterization of the mechanism of the centrifugation-induced TAG production, the *Chlamydomonas* accumulating TAG was also investigated as a material for production of crude bioplastics, uses of which could include the economically sustainable production of biodegradable Mardi Gras beads and other biodegradable plastic items. The present disclosure provides methods for producing the centrifugation-induced TAG production and its application provide methods for sustainable and cost-effective production of crude bioplastics.

Example 1

Materials and Methods
*Chlamydomonas* Strains and Culture Conditions
*Chlamydomonas reinhardtii* strain D66 was obtained from Dr. James Moroney at Louisiana State University. Strains CC-124, 17, and BAFJ5, were obtained from the *Chlamydomonas* Resource Center. *Chlorella vulgaris* was obtained from Culture Collection of Autotrophic Organisms in Czech Republic (Stock #: CCALA 924). *Chlamydomonas* strains and *Chlorella* strain were cultured in 250 mL flasks containing 100 mL TAP, Tris-acetate-phosphate, medium (Gorman & Levine [15], 1965) and BBM medium (Bold [16], 1949), (both incorporated herein by reference). The cultures were kept at 23±2° C. under fluorescence light (60 µmol/m$^2$/s) and constantly shaken on an orbital shaker at 180 rpm. Every 7 days, 100 µl of the culture solution was transferred to a freshly prepared 100 ml medium. When *Chlamydomonas* or *Chlorella* was subjected to centrifugation-induced TAG productions, 10 ml of the 7 days old culture was collected in a 15 ml conical screw cap centrifuge tube (USA Scientific, CAT #1475-0511). The tube was centrifuged at 4,000 g for 5 min. The tube with the cap was left on a laboratory bench at room temperature after supernatant was decanted and remained precipitate. When *Chlamydomonas* was subjected to nitrogen or nutrient starvation, the cells in the 7 days old culture were transferred to a 250 mL flask containing 100 mL TAP-N medium (nitrogen resources were removed from the TAP medium) or 100 ml of water, respectively. When *Chlamydomonas* was subjected to oxygen deficiency, *Chlamydomonas* was first cultured in 100 ml of TAP medium for 7 days. One third of the cells were then transferred to a 250 mL flask containing 30 ml of TAP medium. The culture was bubbled with compressed nitrogen (UN1066) to purge oxygen from the medium.

Counting Cell Numbers
The number of cells in cultures was counted using a hemocytometer (Hausser Scientific Partnership) after the cells were immobilized with 150 mM of potassium chloride.

Lipid Extraction
The previously published method was followed (Kato et al., 2013 [14], incorporated herein by reference). Briefly, *Chlamydomonas* cells in the 10 ml culture were re-suspended in a solution containing 1 mL of 50 mM dipotassium phosphate, 2 mL of methanol and 1 mL of chloroform and vortexed. The organic phase was transferred into a 2 mL microcentrifuge tube, and the organic solvent was evaporated.

Carotenoids Extraction
*Chlamydomonas* cells in the 10 ml culture were re-suspended in 2 ml diethyl ether, the solvent. The resulting mixture was vortexed and centrifuged at 4,800 g for 2-3 min. The supernatant was then collected. The extraction was repeated 3 times. The supernatants from each extract were collected in a 15 ml conical tube and heating it at 70° C. to evaporate the solvent.

Thin Layer Chromatograph (TLC) Analysis
The previously published method was followed for triacylglycerol analysis [14]. Briefly, the extracted lipids were analyzed on a 250 µm layer silica plate (Whatman) in a TLC tank that consisted of 220 mL hexane, 80 mL diethyl ether and 1 mL glacial acetic acid. Triacylglycerols were visualized by charring the plate with 1 N sulfuric acid, Amounts of triacylglycerols in samples were calculated by scanning the charred plate through a scanner (EPSON 4180 PHOTO) and quantifying intensities of spots through FIJI imaging software. Spots of triolein (Sigma-Aldrich) where 5 µg, 10 µg, and 25 µg were applied, respectively, were used to generate a standard curve. When carotenoids were analyzed, the extracted carotenoids were dissolved in diethyl ether and spotted on a 250 µm layer silica plate (Mikami & Hosokawa [17], incorporated herein by reference). The plate was then developed in a TLC tank that consisted of 210 ml petroleum ether and 90 ml acetone. Lutein (CVS pharmacy) was used as a standard.

Transmission Electron Microscopy Analysis
The previously published method was followed [14]. Briefly, 1 mL aliquot of culture was transferred to 1.5 mL microcentrifuge tubes (USA Scientific). The tubes were centrifuged to harvest the cells and the cells were fixed, sliced and imaged.

Fatty Acid Methyl Esters (FAME) Analysis
Triacylglycerol spots in a TLC plate were scraped and eluted with hexane. The FAMEs were prepared and analyzed by gas chromatography-flame ionization detector (GC-FID) as described in Siaut et al. [11] (herein incorporated by reference).

Algal Bead Molding
*Chlamydomonas* and *Chlorella* were cultured in 2 L flasks containing 1 L culture medium, TAP and BBM, respectively. The cultures were kept at 23±2° C. under fluorescence light (60 µmol/m$^2$/s) and constantly shaken on an orbital shaker at 180 rpm. The culture was centrifuged in 4×250 ml centrifuge bottles (Nalgene) at 4,000 g for 5 min. The bottles with the cap were left on a laboratory bench at room temperature after the supernatant was decanted. The biomass (0.1 g each) of *Chlamydomonas* and *Chlorella* were mixed on a microscope slide (Corning 294875X25) and 10% (weight/dry weight biomass) of ammonium persulfate or glycerol was mixed. The biomass was autoclaved at 121° C. for 20 min. The biomass was then molded into beads manually. The beads were left at room temperature overnight.

Compressive Strength Test on Beads
Compressive strength test was conducted with Material Testing System Model 810 (MTS Systems Corporation). The vertical compression load was applied to each bead with a compression rate at 0.02 mm/sec. The applied force in megapascal (MPa) was continually monitored with the TestWare-SX software.

Results and Discussion

A Protocol of Centrifugation-Induced Triacylglycerol Production was Established
During a time course experiment for *Chlamydomonas* triacylglycerol (TAG) production [14], it was unexpectedly found that *Chlamydomonas* accumulated TAG when a centrifuged biomass was accidentally left in a tube overnight at room temperature. Based on the finding, a protocol was established in which 10 ml of 7 days old culture was subjected to centrifugation-induced TAG production (FIG. 1). The steps of an embodiment of centrifuge-induced TAG production shown in FIG. 1 are as follows: (1) *Chlamydomonas* is cultured in a 250 ml flask containing 100 ml TAP medium with 12 h/12 h (light/dark) light condition for 7 days. (2) Ten milliliter of the culture is transferred to a 15 ml centrifuge tube. (3) The transferred culture is centrifuged at 4,000 g for 5 min. The supernatant is discarded. (4) The precipitate (ppt) is left on a laboratory bench for 24 h (overnight) at room temperature (RT). The protocol can be applied to a larger amount of culture (i.e., 1 L) as described in Materials and Methods.

Figure 2A:
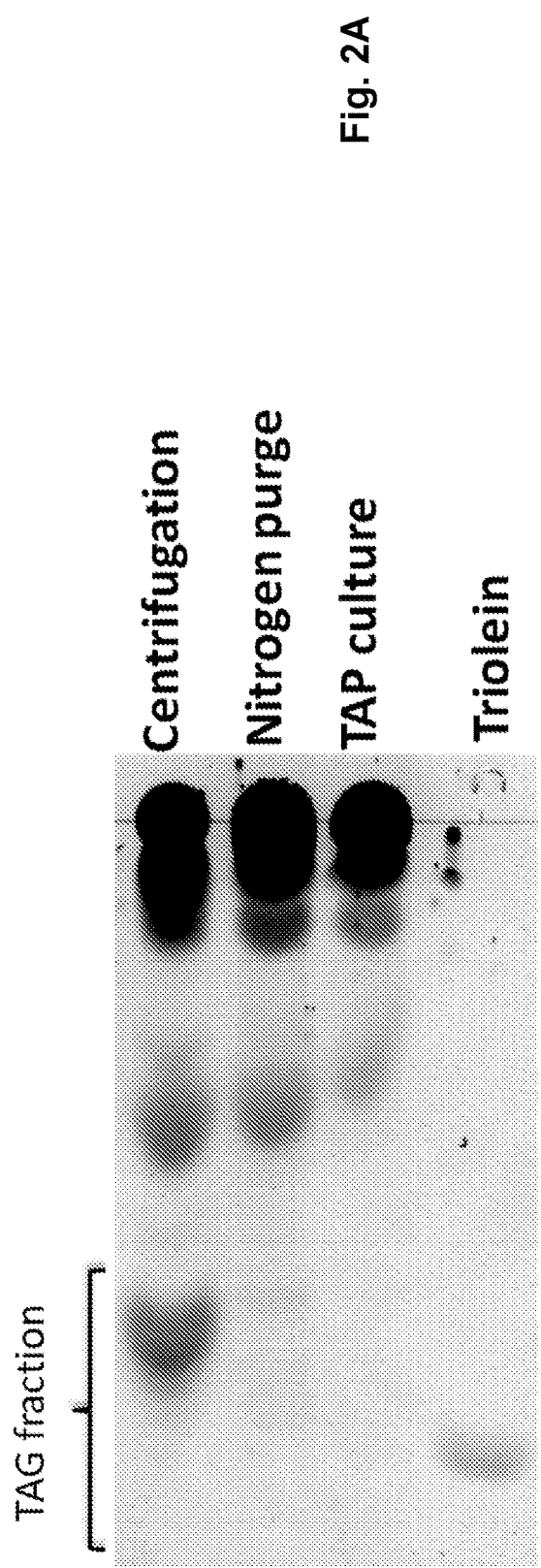
FIGS. 2A-B illustrate that triacylglycerol production is induced by centrifugation but not by lack of nutrients or oxygen.
Figure 2B:
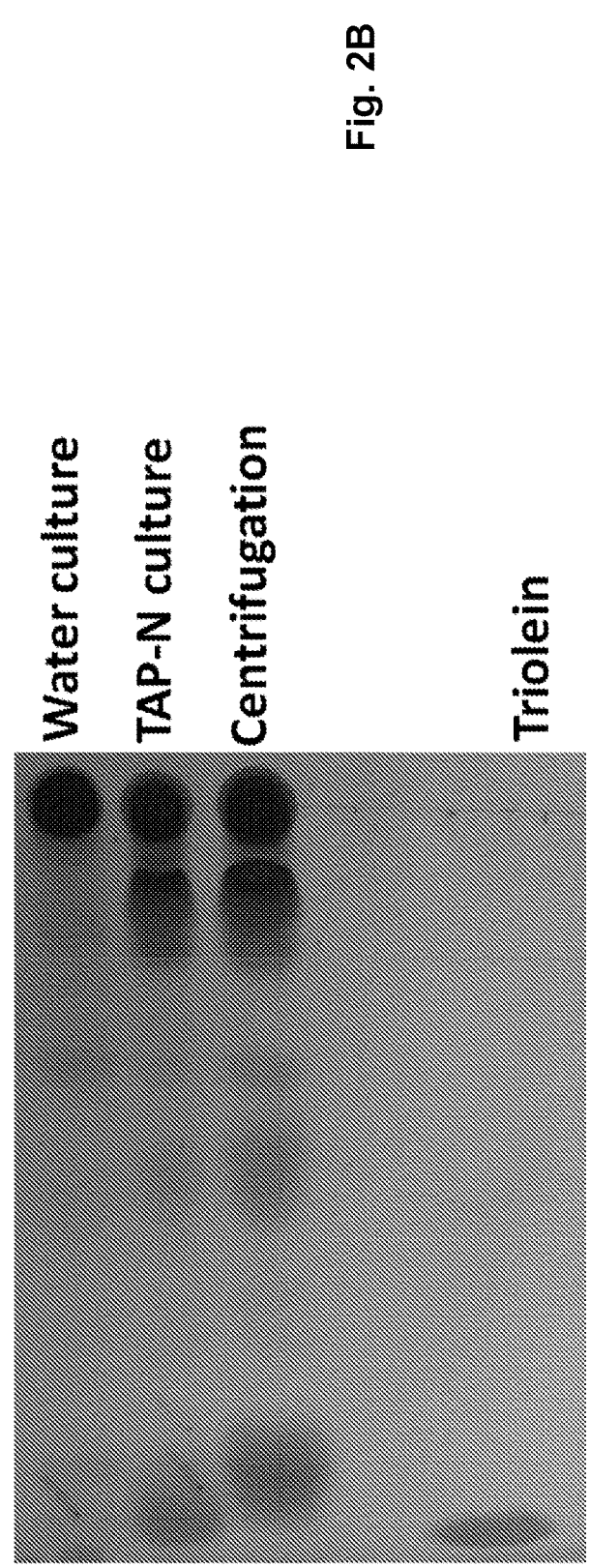

Triacylglycerol Production is Induced by Centrifugation but not by Lack of Nutrients or Oxygen The amount of TAG accumulated in *Chlamydomonas* subjected to the centrifugation-induced TAG production was compared to the amount of TAG accumulated in *Chlamydomonas* subjected to nitrogen starvation, which is known to induce the TAG production in *Chlamydomonas* [11] (FIG. 2A). FIG. 2A shows TLC analysis of triacylglycerol. *Chlamydomonas* D66 was first cultured in 100 ml of TAP medium for 7 days. Lane Triolein: 5 μg of triolein, triacylglycerol standard. Lane centrifugation: Ten milliliter of the culture was centrifuged and left for 24 h. Lane TAP-N culture: The culture was transferred to the TAP-N medium to culture for 24 h. Lane Water culture: The culture was transferred to water (total limitation of nutrients) and cultured for 24 h. The biomass equal to $10^6$ cells were analyzed in each lane. The centrifugation-induced and nitrogen starvation *Chlamydomonas* produced 41.7 and 16.3 $\mu g/10^6$ *Chlamydomonas* cells, respectively, 24 h after the process in the experiment. The average amount of TAG in the five independent experiments of the centrifugation-induced and nitrogen starvation *Chlamydomonas* was 55.1±17.0 and 16.2±3.5 $\mu g/10^6$ cells. This result indicates that the centrifuged *Chlamydomonas* produces about 3 times higher amount of TAG than the nitrogen-starved *Chlamydomonas* in the first 24 h. FIG. 2B shows the TLC analysis of triacylglycerol. *Chlamydomonas* D66 was first cultured in 100 ml of TAP medium for 7 days. Lane Triolein: 5 μg of triolein. Lane TAP culture: One-third of the cells were then transferred to 30 ml of TAP medium to culture for 24 h, Lane Nitrogen purge: One-third of the cells were then transferred to 30 ml of TAP medium. The culture was bubbled with nitrogen to purge oxygen from the medium for 24 h. Lane Centrifugation: Ten milliliter of the culture was centrifuged and left for 24 h. The biomass equal to 106 cells were analyzed in each lane.

It was initially believed that *Chlamydomonas* accumulates TAG after centrifugation due to environmental stress, namely lacking nutrients and/or oxygen as previously reported in microalgae [18, 19] and a plant [20], respectively. However, in the above experiment in which *Chlamydomonas* was subjected to total limitation of nutrients (water culture) and oxygen limitation (nitrogen purge) for 24 h showed little production of TAG. This result suggests that limitation of nutrients or oxygen, alone, does not produce TAG efficiently in *Chlamydomonas*.

Figure 3:
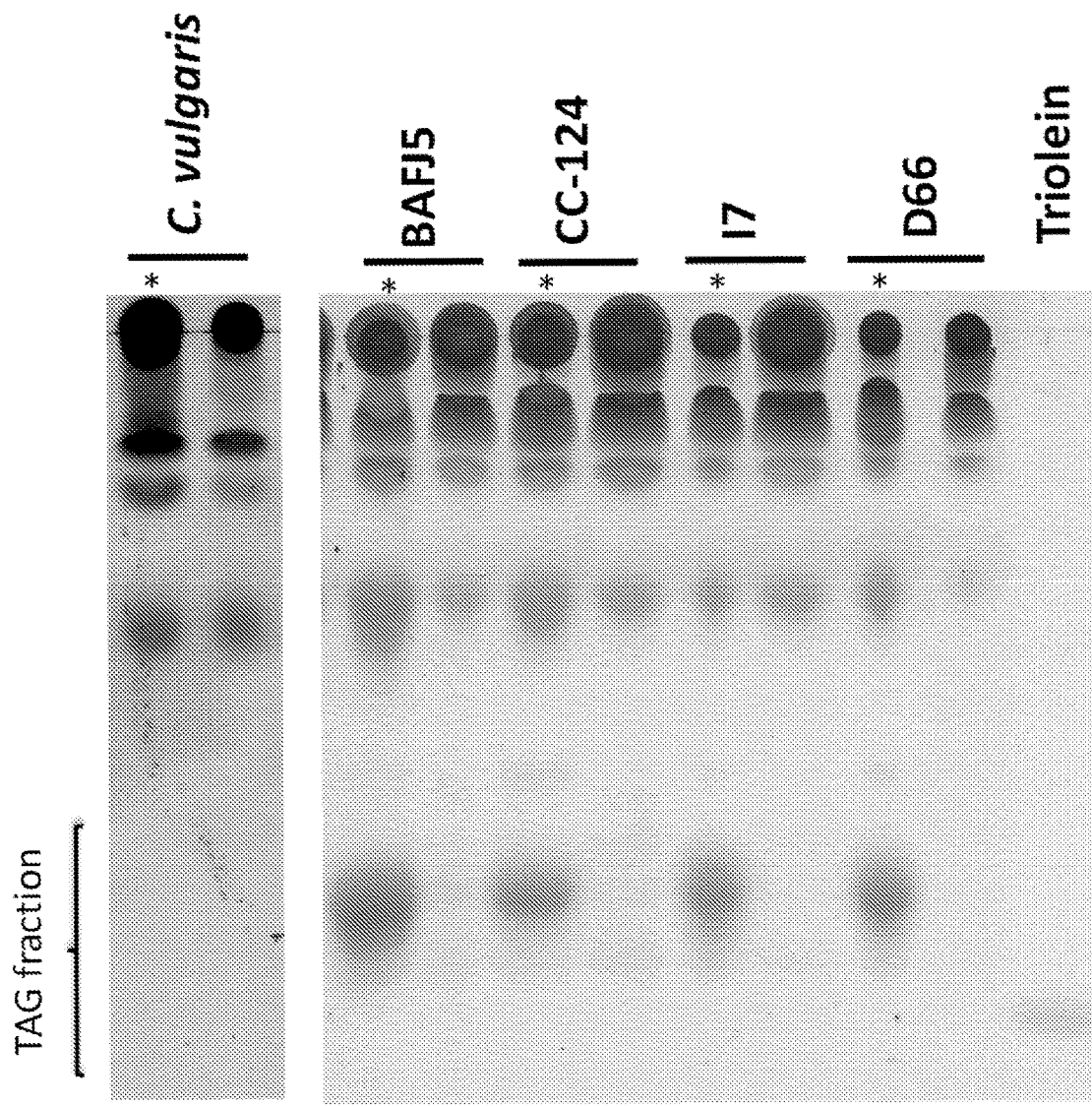
FIG. 3 illustrates that centrifugation induces triacylglycerol production in *Chlamydomonas* strains but not in a *Chlorella* strain.

Centrifugation Induces Triacylglycerol Production in *Chlamydomonas* Strains but not in a *Chlorella* Strain The *Chlamydomonas* strain originally used for the centrifugation-induced TAG production was a mutant strain, D66, that lacks cell wall [14]. To investigate the effect of *Chlamydomonas* mutations in the centrifugation-induced TAG production, several different mutant strains were analyzed, namely 17 and BAFJ5, which lack production of starch [11], as well as CC-124, which lacks unknown-functional protein AGG1 [21]. Analysis of *Chlorella vulgaris* [22] was also performed to understand whether the centrifugation-induced TAG production is commonly observed in the Chlorophyta taxonomic division. Our TLC analysis using samples 24 h after centrifugation revealed that all *Chlamydomonas* mutant strains produce a similar amount of TAG while *C. vulgaris* does not produce TAG (FIG. 3). FIG. 3 shows TLC analysis of triacylglycerol. *Chlamydomonas* strains, D66 (cw15, nit1, mt$^+$), 17 (sta1-1, nit1, nit2, mt$^-$), CC-124 (agg1, nit1, nit2, mt$^-$), BAFJ5 (sta6-1, cw15, nit1, nit2, arg7-7, sta6-1::ARG7 mt$^+$), and a *Chlorella* strain (*Chlorella vulgaris*) were subjected to centrifugation-induced triacylglycerol production. The biomass equal to $10^6$ cells were analyzed in each lane, Lane Triolein: 5 μg of triolein. * indicates a centrifuged sample. This finding suggests that centrifugation-induced TAG production occurs in a selected taxonomic genus.

A previous report indicates that applying 10-15 bar pressure for 2 h on *C. vulgaris* induces TAG production [23]. This suggests that centrifugation does not provide the pressure stress on the cells. On the other hand, another previous report indicates that compressive distortion of a single *Chlamydomonas* cell by a microfluid device induces TAG production [24]. This suggests that cells may not perceive all stresses similarly to induce TAG production. Further study may elucidate how Chlorophyta organisms (i.e., *Chlamydomonas* and *Chlorella*) perceive pressure and compressive stresses differently.

Figure 4A:
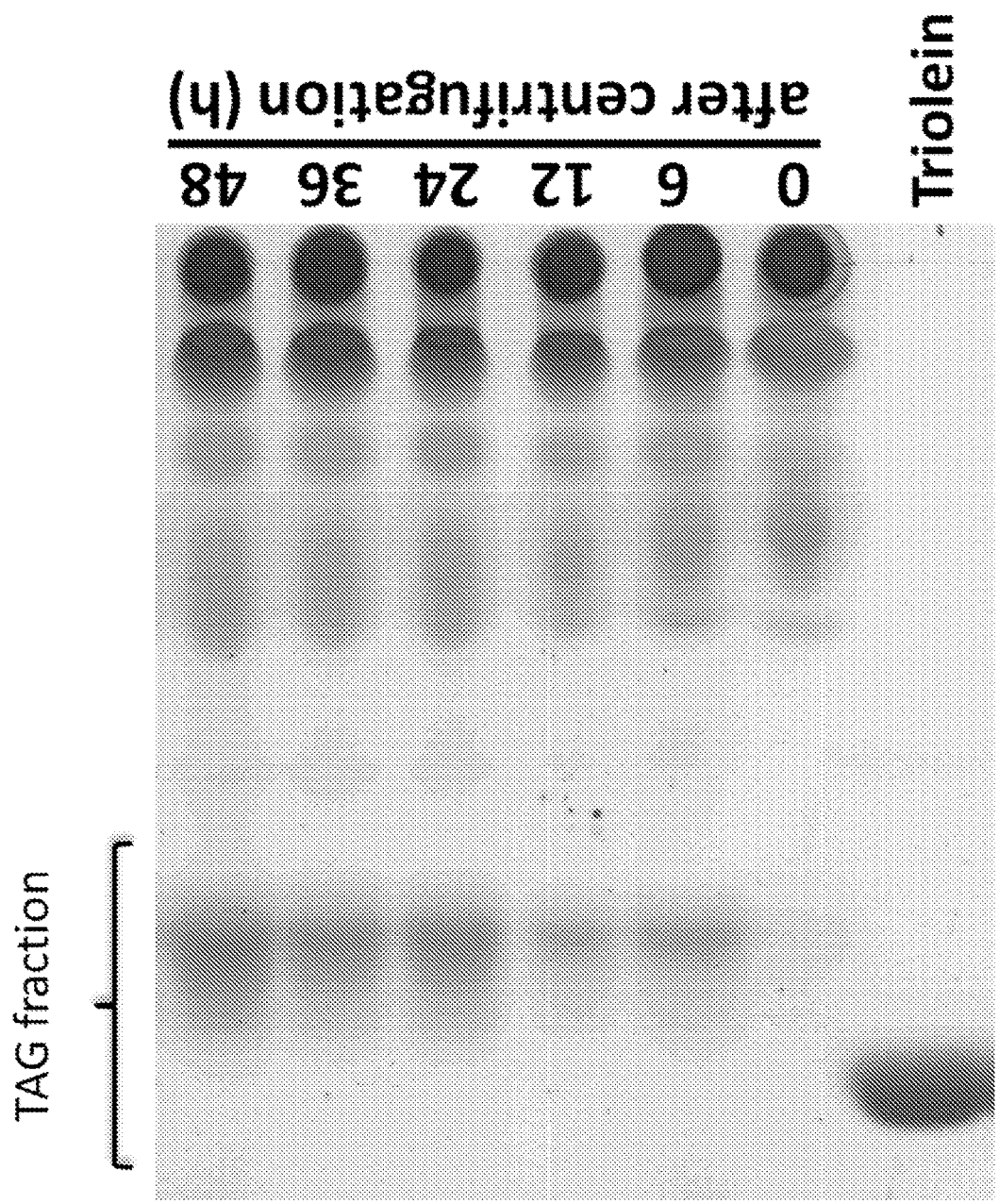
FIGS. 4A-B illustrate that centrifugation induces the triacylglycerol production within 6 h while it does not alter the carotenoid production.

Centrifugation Induces the Triacylglycerol Production within 6 h while it does not Alternate the Carotenoid Production To investigate the kinetics of the TAG production after centrifugation, a time-course experiment was conducted in which samples were collected at certain time points within 48 h after centrifugation (FIG. 4A). FIG. 4A shows TLC analysis of triacylglycerol. *Chlamydomonas* D66 was first cultured in 100 ml of TAP medium for 7 days. 10 ml of cultures were centrifuged, individually, and left on a laboratory bench. The samples are collected 0, 6, 12, 24, 36, and 48 h after the centrifugation. The biomass equal to $10^6$ cells were analyzed in each lane. Lane Triolein: 25 μg of triolein. TLC analysis found that TAG is produced within 6 h after centrifugation, and the TAG production level reaches the maximum 24 h after centrifugation. The produced TAG was not degraded (or production/degradation rate was not changed) 48 h after centrifugation.

Figure 4B:
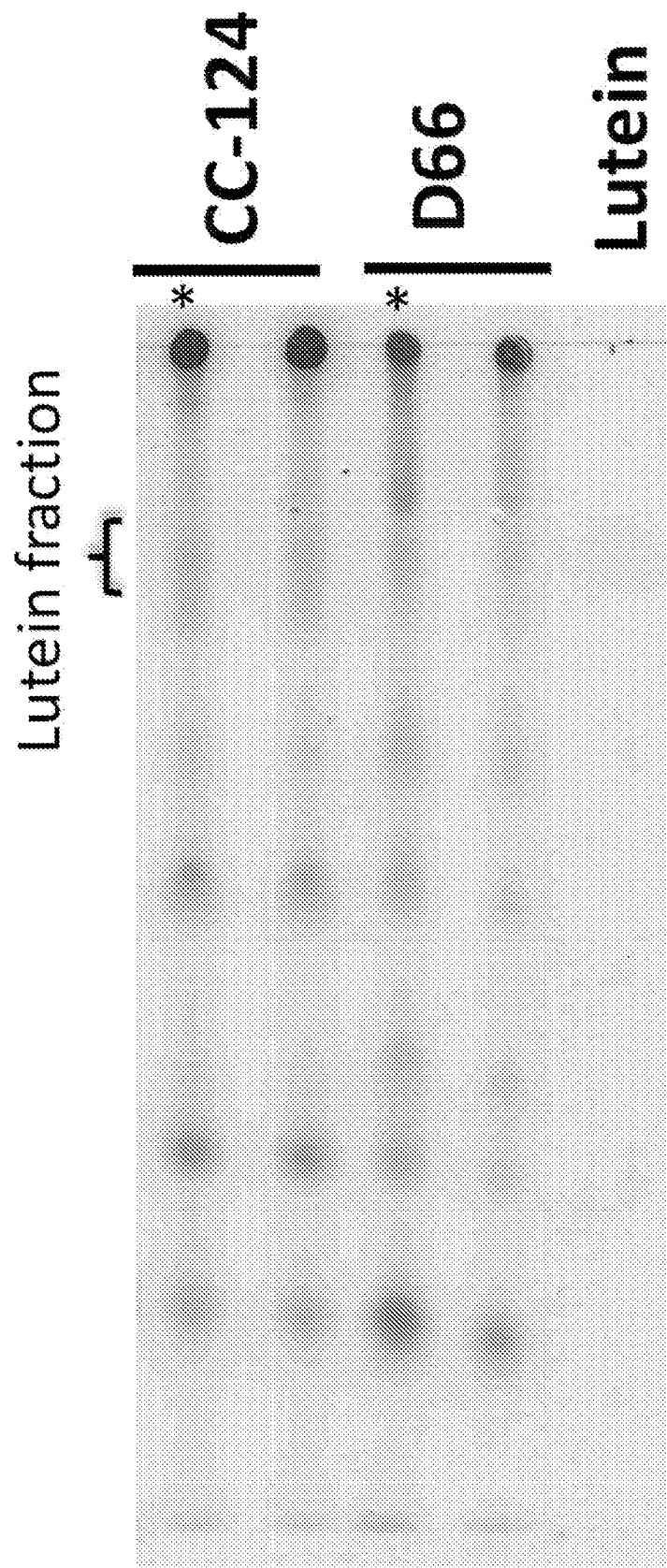

Because a previous study indicated that carotenoid production has a negative correlation with the TAG production in microalgae [25], changes in carotenoid production in *Chlamydomonas* subjected to the centrifugation-induced TAG production were investigated. TLC analysis found that the carotenoid production, which can be identified as yellow spots on the TCL plate [17], are not changed qualitatively during centrifugation-induced TAG production (FIG. 4B). FIG. 4B shows TLC analysis of carotenoids. The samples, *Chlamydomonas* D66 and CC-124, at 48 h after the centrifugation were subjected to the carotenoid analysis. The biomass equal to $10^6$ cells were analyzed in each lane, Lane Lutein: Purified lutein.

This suggests that centrifugation does not affect carotenoid synthetic pathway while it upregulates the TAG synthetic pathway. From an applied science point of view, this also suggests that co-productions of lutein, which is a commercially valuable compound, in *Chlamydomonas* [26, 27] and TAG would be possible with centrifugation.

Centrifugation-Induced Triacylglycerol Production Disrupts the Chloroplast Membranes

Figure 5B:
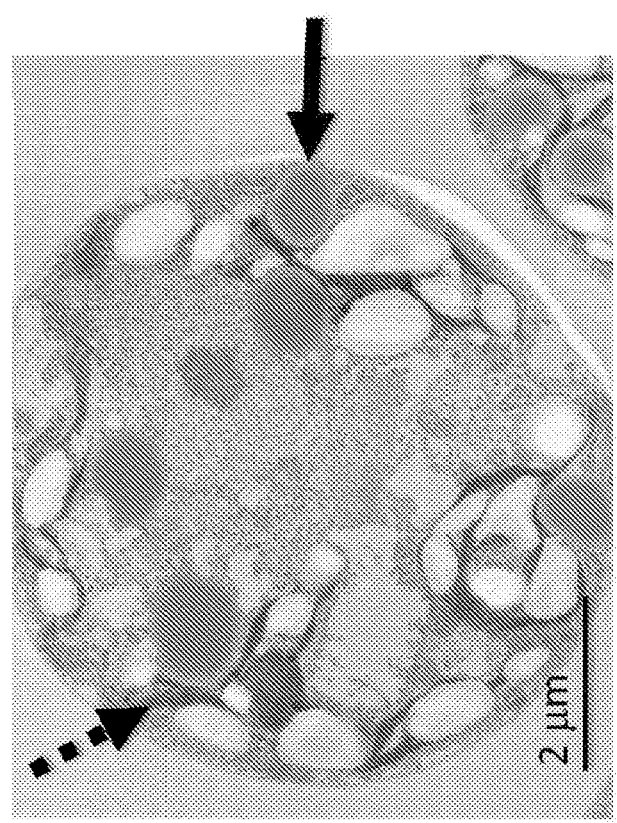
FIGS. 5A-B show that centrifugation-induced triacylglycerol production disrupts the chloroplast membranes.
Figure 5A:
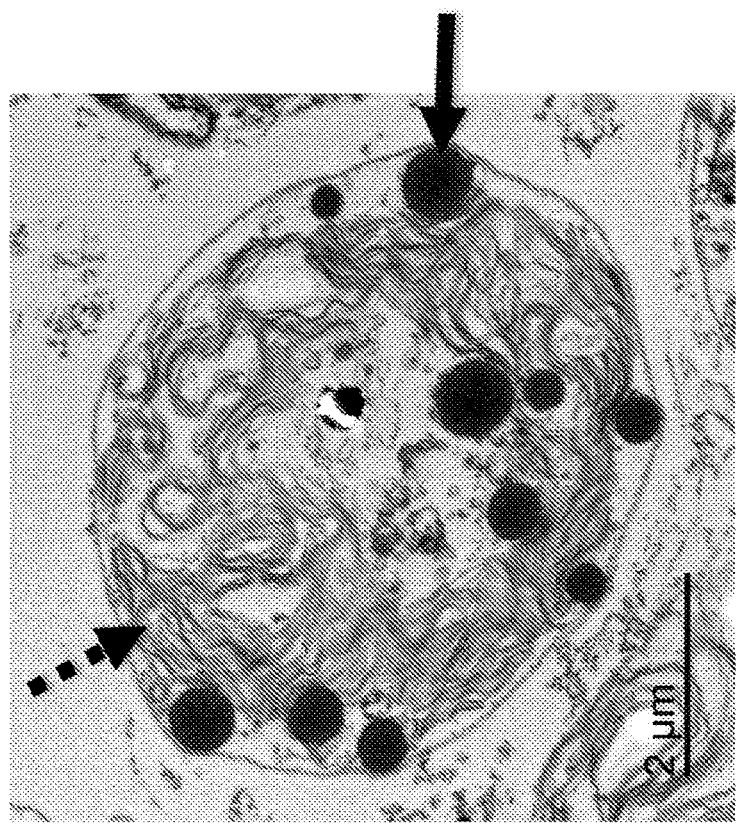

*Chlamydomonas* gradually accumulates TAG in the lipid droplets, organelles composed of a single layer of phospholipid, for 5 to 7 days when it is exposed to a nitrogen-depletion condition [28], To investigate the localization where rapidly produced TAG is accumulated by the centrifugation, transmission electron microscopy was conducted (FIGS. 5A-B). FIG. 5A shows a cell of *Chlamydomonas* D66 subjected to centrifugation-induced triacylglycerol for 24 h, observed by a transmission electron microscope. Solid and dashed arrows indicate the lipid droplet and chloroplast membranes, respectively. Note that the chloroplast membranes are largely disturbed. FIG. 5B shows a cell of *Chlamydomonas* D66 cultured in TAP-N medium for 4 d, observed by a transmission electron microscope. Solid and dashed arrows indicate the lipid droplet and chloroplast membranes, respectively. Note that the chloroplast membranes are tight. Electron-dense organelles proximate to the chloroplast in *Chlamydomonas* that were subjected to the centrifugation-induced TAG production for 24 h, similar to *Chlamydomonas* subjected to nitrogen depletion for 4 days. This indicates that TAG rapidly synthesized by centrifugation is accumulated in the lipid droplets. Chloroplast membranes in the centrifuged *Chlamydomonas* were largely disrupted, which is not found in those in the nitrogen-depleted *Chlamydomonas*. This indicates that centrifugation and nitrogen-depletion may stress *Chlamydomonas* differently although both stresses induce the TAG production.

Figure 6:
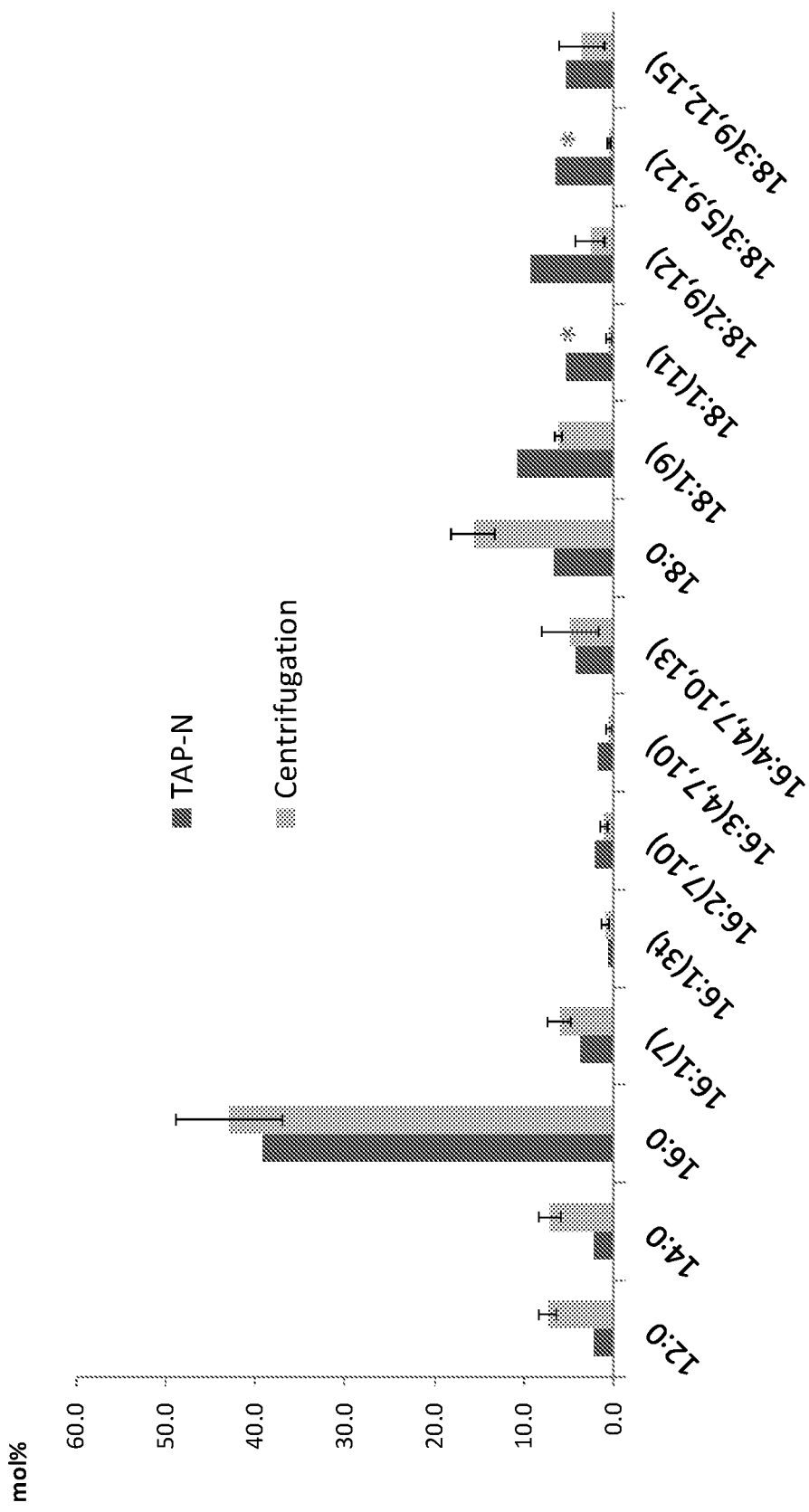
FIG. 6 demonstrates that triacylglycerols induced by centrifugation rarely contain C18:1 (11) and C18:3 (5,9,12) fatty acids.

Triacylglycerol Produced by Centrifugation Contains Trivial Amounts of C18:1 (11) and C18:3 (5,9,12) Fatty Acids Rapid accumulation of TAG and disruption of the chloroplast membranes are prominent differences between centrifuged and nitrogen-depleted *Chlamydomonas* (FIGS. 2A-B and 5A-B). To understand the difference in TAG molecules, analysis of fatty acids esterified in TAG that had accumulated in the *Chlamydomonas* was performed, where the *Chlamydomonas* had been subjected to the centrifugation-induced TAG production for 24 h (FIG. 6). Triacylglycerol fractions of silica gel in the thin layer chromatography were scraped and subjected to fatty acid methyl esters analysis. Three biological replications of centrifugation-induced *Chlamydomonas* and one biological replicate of TAP-N medium-cultured *Chlamydomonas* were used for the analysis. FAME (fatty acid methyl esters) analysis detected only 0.53±0.28 and 0.51±0.17% (mol/mol) of C18:1 (11) and C18:3 (5,9,12) fatty acid, respectively, in three independent experiments. These fatty acids are extrachloroplast lipids, present in cellular membranes, except the chloroplast, and incorporated in TAG during nitrogen depletion [29]. TAG synthesized during nitrogen depletion normally contains about 5-10% of C18:1 (11) and C18:3 (5,9,12) fatty acids, respectively [19, 29-31]. In the present experiment, the TAG prepared from *Chlamydomonas* subjected to nitrogen depletion for 4 days contains 5.42 and 6.41% of C18:1 (11) and C18:3 (5,9,12) fatty acid, respectively. This confirmed that the low-level detections of C18:1 (11) and C18:3 (5,9,12) fatty acids were not due to errors that might occur during the sample or standard preparation.

Together with the result from transmission electron microscopy (FIGS. 5A-B), it is possible that the centrifuged *Chlamydomonas* disassembles the chloroplast membranes, and the fatty acids in the membranes are incorporated into TAG. Unlike the TAG production induced by other stresses such as nitrogen depletion, in which fatty acids from both the chloroplast and endoplasmic reticulum membranes are incorporated into TAG [29, 31], the TAG production induced by centrifugation may rarely incorporate fatty acids from the endoplasmic reticulum membrane.

Moreover, the FAME analysis revealed TAGs synthesized by centrifugation contain more saturated fatty acids than that synthesized in stress conditions (FIG. 6). For example, FAME analysis detected 7.15+1.24 and 15.69+2.43% (mol/mol) of C14:0 and C18:0 fatty acid, respectively, in our three independent experiments. On the other hand, a previous study showed that TAGs synthesized during nitrogen depletion contain, 0.7+0.0 and 2.7+0.2% (mol/mol) of C14:0 and C18:0 fatty acid, respectively [29]. Biodiesel containing highly unsaturated fatty acids are not suitable as fuel [39]. On the other hand, intake of TGAs rich in saturated fatty acids may increase incidence of cardiovascular disease [40]. Hence, the fatty acid contents define the usage and commercial value of TAGs. Normally, researchers screen microalgae that produce TAGs suitable for each usage (i.e., biofuel, biopolymers, human consumption, etc.). However, the identified microalga is often not suitable for a large-scale cultivation. In another case, a microalga that is suitable for a large-scale cultivation does not produce TAGs that are suitable for usage such as described herein. Genetic modification may be one way to control fatty acid contents in TAGs as previous studies showed the potential [36, 37]. The present disclosure provides another way to alter fatty acid contents in TAGs as the studies described herein showed that the fatty acid contents in TAGs can be modified by centrifuging microalgal biomass. Said modified fatty acid contents in TAGs as described herein can be used for biofuels, biopolymers, and human consumption.

Centrifuged *Chlamydomonas* Biomass can Form Crude Bioplastics

Figure 7:
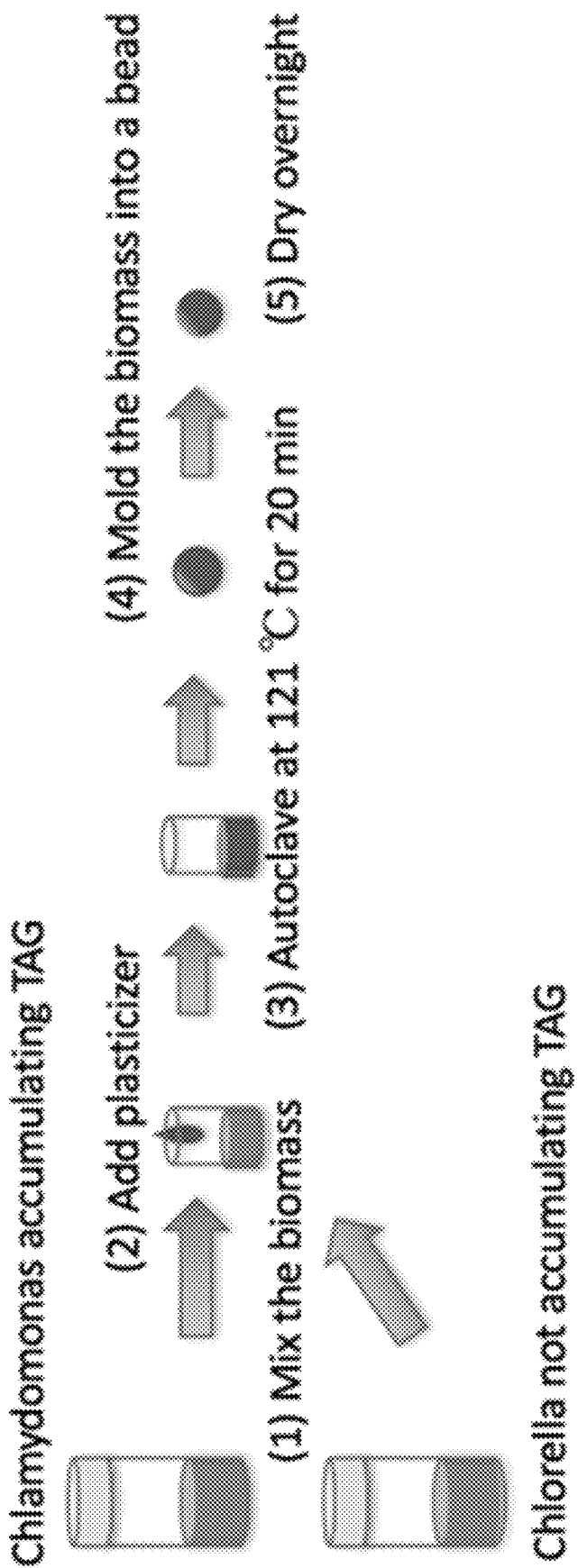
FIG. 7 illustrates an embodiment of a process by which centrifuged *Chlamydomonas* biomass can be plasticized with other algal biomass to mold beads.

The present disclosure provides a protocol that allows formation of molded beads directly from the *Chlamydomonas* biomass accumulating TAG (FIG. 7). The protocol includes the steps: (1) Centrifuged *Chlamydomonas* biomass accumulating triacylglycerol (TAG) is mixed with centrifuged *Chlorella* biomass not accumulating TAG; (2) Plasticizer is added to promote flexibility or to reduce brittleness; (3) The mixed biomass is heated to promote covalent bounds among compounds in the biomass; (4) The biomass is molded into a bead manually; (5) The bead is air-dried overnight.

For the proof-of-concept, 1 L culture of *Chlamydomonas* D66 was used. A mixed 1 L culture of the *Chlorella vulgaris* was also used that was subjected to centrifugation-induced TAG production. As found in the experiment (FIG. 3), *C. vulgaris* does not accumulate TAG through the process. Yet, it was rationalized that the compounds in the biomass such as starch can contribute to the crosslinking of the molecules within the mixed biomass. As an oxidizing agent, 10% (w/d·w. biomass) of ammonium persulfate was added. To enhance the radical production and crosslinking among the molecules in the biomass; the biomass containing the additive was also autoclaved. The autoclaved biomass was then molded into beads manually and air-dried overnight at room temperature.

Algal Beads Maintain Strength

Figures 8A, 8B:
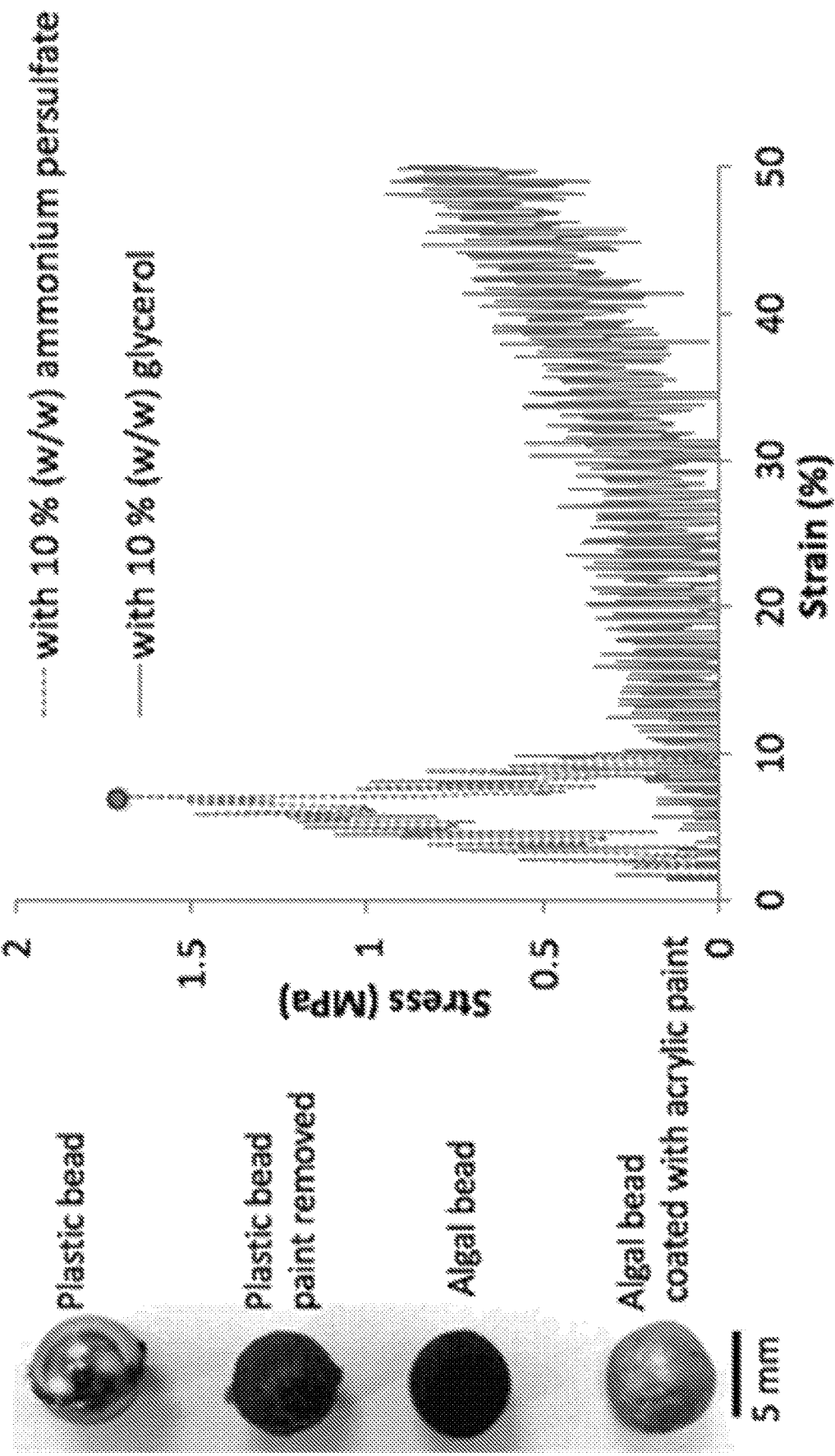
FIGS. 8A-B illustrate that beads formed from algae maintain strength when subjected to strain.

The appearance and physical strength of the molded beads (algal beads), were compared to petroleum-based Mardi Gras beads thrown by a krewe during a Mardi Gras parade in Louisiana (FIG. 8A). Individual beads were detached from the threaded Mardi Gras beads and the paint removed. The beads were then compared to the algal beads that were molded manually. The appearance between the beads was almost indistinguishable, although the shape of the algaplastic beads was not perfectly spherical due to manual molding. The algal beads can be painted manually, based on the present experiment. A compressive strength test revealed the point (1.70 MPa, 7.00% strain) where the algal bead cracks (FIG. 8B). FIG. 8B compares the compressive strength of the algal beads plasticized and molded with 10% (w/d·w. biomass) ammonium persulfate and 10% (w/d·w. biomass) glycerol, respectively. The dashed line indicates the result of an algal bead (5.5 mm in diameter, no paint) molded with 10% (w/d·w. biomass) ammonium persulfate, the radical producer. The solid line indicates the result of an algaplastic bead (6.95 mm in diameter, no paint) molded with 10% (w/d·w. biomass) glycerol, the plasticizer.

The same test with the petroleum-based Mardi Gras bead revealed the cracking point is 12.08 MPa (24.7% strain). These suggest that the strength of the algal bead is about 14% of that made from the petroleum and similar to mud bricks that are used for non-industrial constructions [32]. This indicates that the algal beads maintain certain physical strengths when they are molded with ammonium persulfate. When the algal bead is molded with 10% (w/d·w. biomass) of glycerol, the stress and strain are linearly correlated, but the slope is much lower than that with ammonium persulfate. This indicates that the bead is elastic and suggests that adding a different additive in the biomass could change the physical characteristics of the final products.

Although the algal beads generated in this study may not be strong enough for industrial use, they may be sufficient for use in applications such as MOT beads and other uses with further research development. As shown in this study, microalgae produce both commercially valuable carotenoids (FIG. 4) and biopolymers that can be used for crude bioplastics (FIGS. 8A-B). Co-production of carotenoids and crude bioplastics is proposed herein to increase economic competitiveness against petroleum-based plastics.

Example 2

Figure 10A:
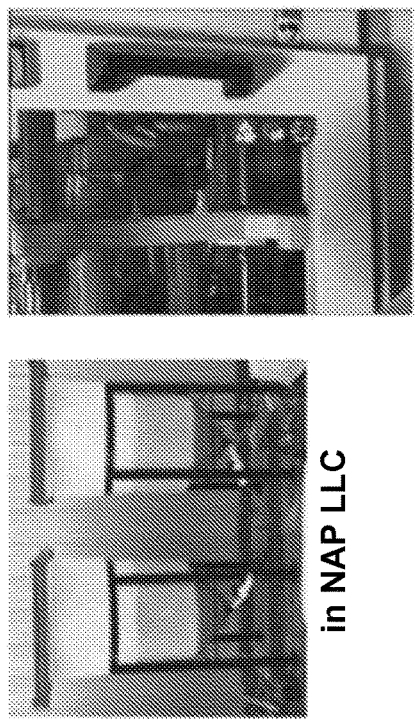
FIGS. 10A-D illustrate properties and production of alga-mixed plastics including polyethylene.
Figure 10B:
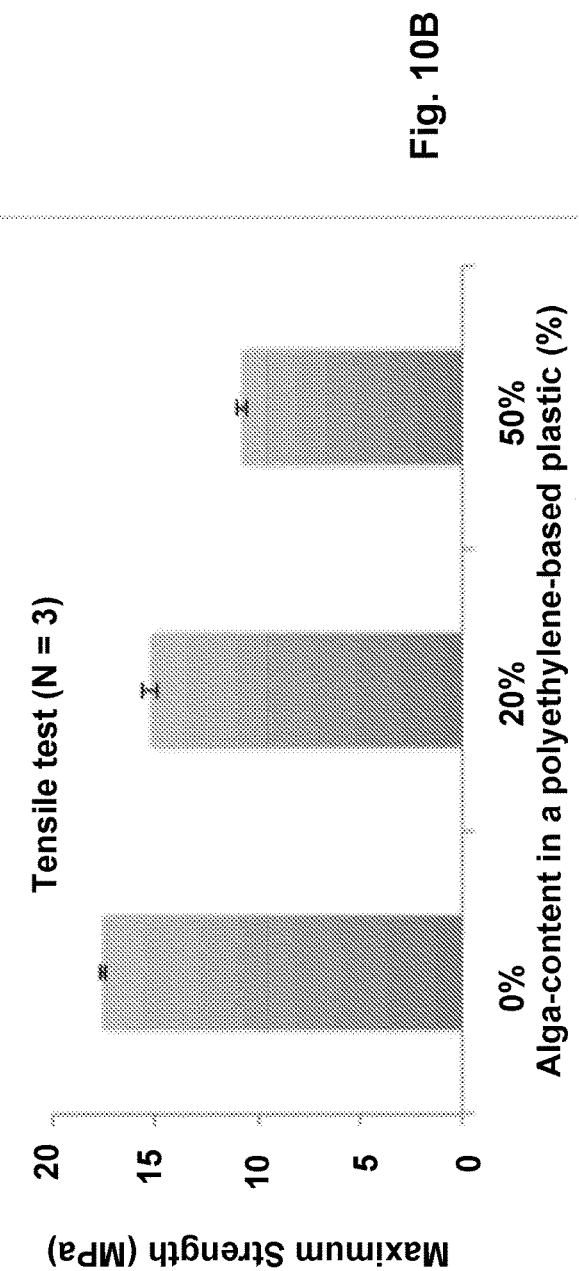
Figure 10C:
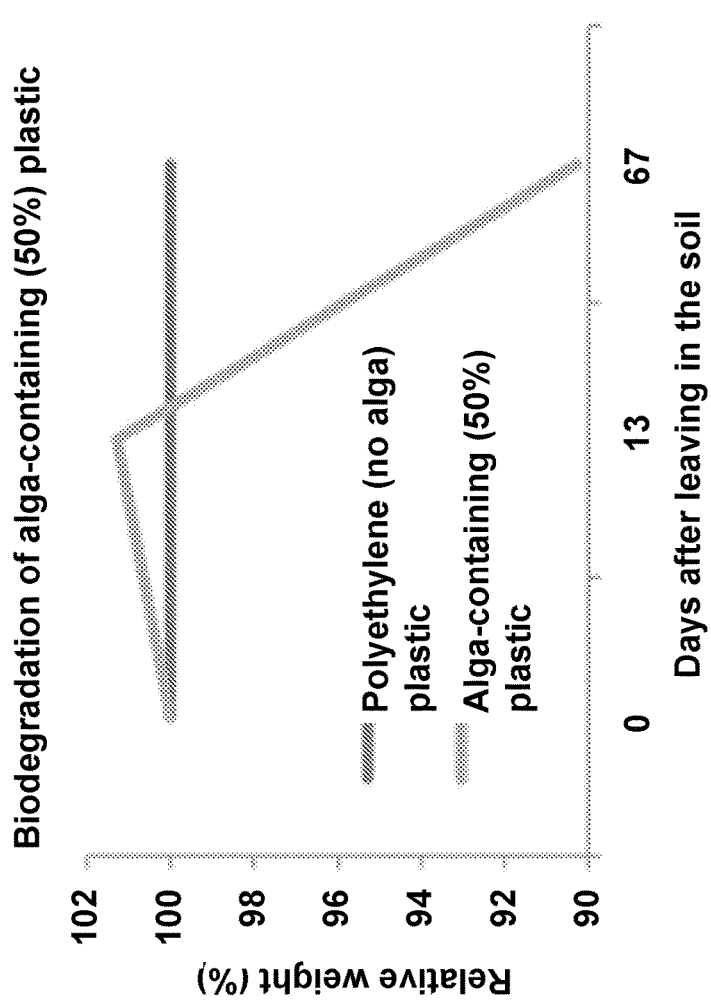
Figure 10D:
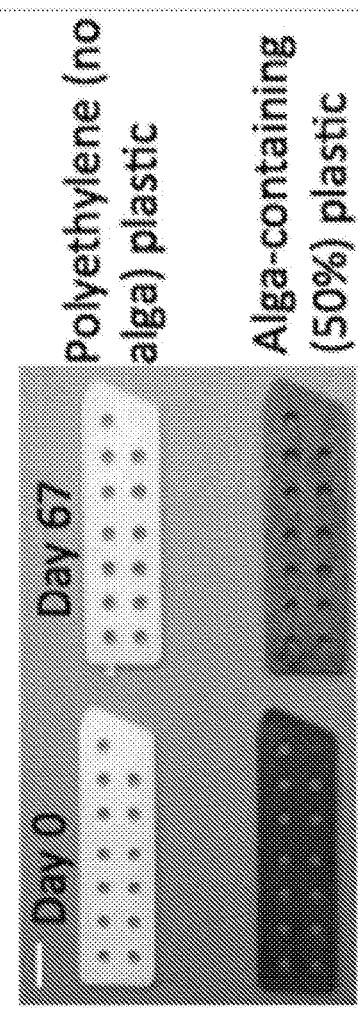
Figure 11:
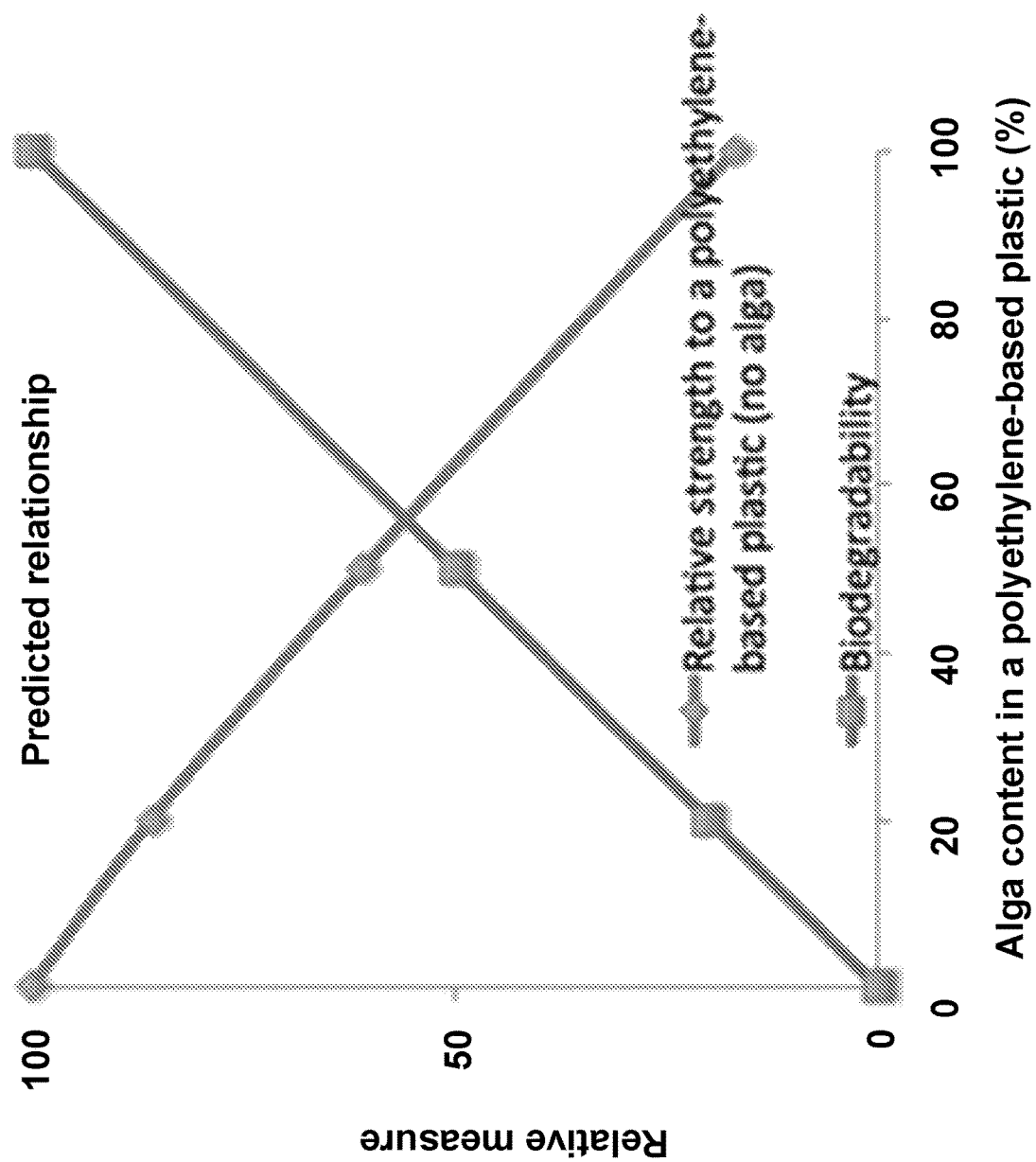
FIG. 11 illustrates the predicted relationship among alga content, strength, and biodegradability of bioplastics containing varying ratios of alga to polyethylene.

It was also found that the algaplastics can be mixed with polyethylene, a conventional plastic, to produce alga-mixed plastics (FIGS. 10A-D). Algae biomass was cultured in tanks (FIG. 10A, left) and extrusion-molded (FIG. 10A, right). As shown in FIG. 10B, a tensile test revealed the strength of the bioplastics. Of note is that the bioplastic containing 50% of algal biomass has 60% of strength compared to a polyethylene-based plastic. Biodegradation of the alga-containing plastic was confirmed (FIG. 10C). The bioplastic containing 50% of algal biomass lost 10% of the weight while the polyethylene-based plastic lost none within 70 days in the soil. The effects of biodegradation of the alga-containing plastic were also visually analyzed, indicated by a change of colors (FIG. 10D). Based on the data presented in the present example, the relationship between the strength, biodegradability, and biomass in the algaplastics could be predicted (FIG. 11). The prediction is based on the data obtained in the previous analysis and in FIG. 12. We predicted strength of the bioplastics is negatively and linearly related to the content (% w/w) of algal biomass. We also predicted biodegradability is positively and linearly related to the content (% w/w) of algal biomass.

Example 3

Figures 12A, 12B:
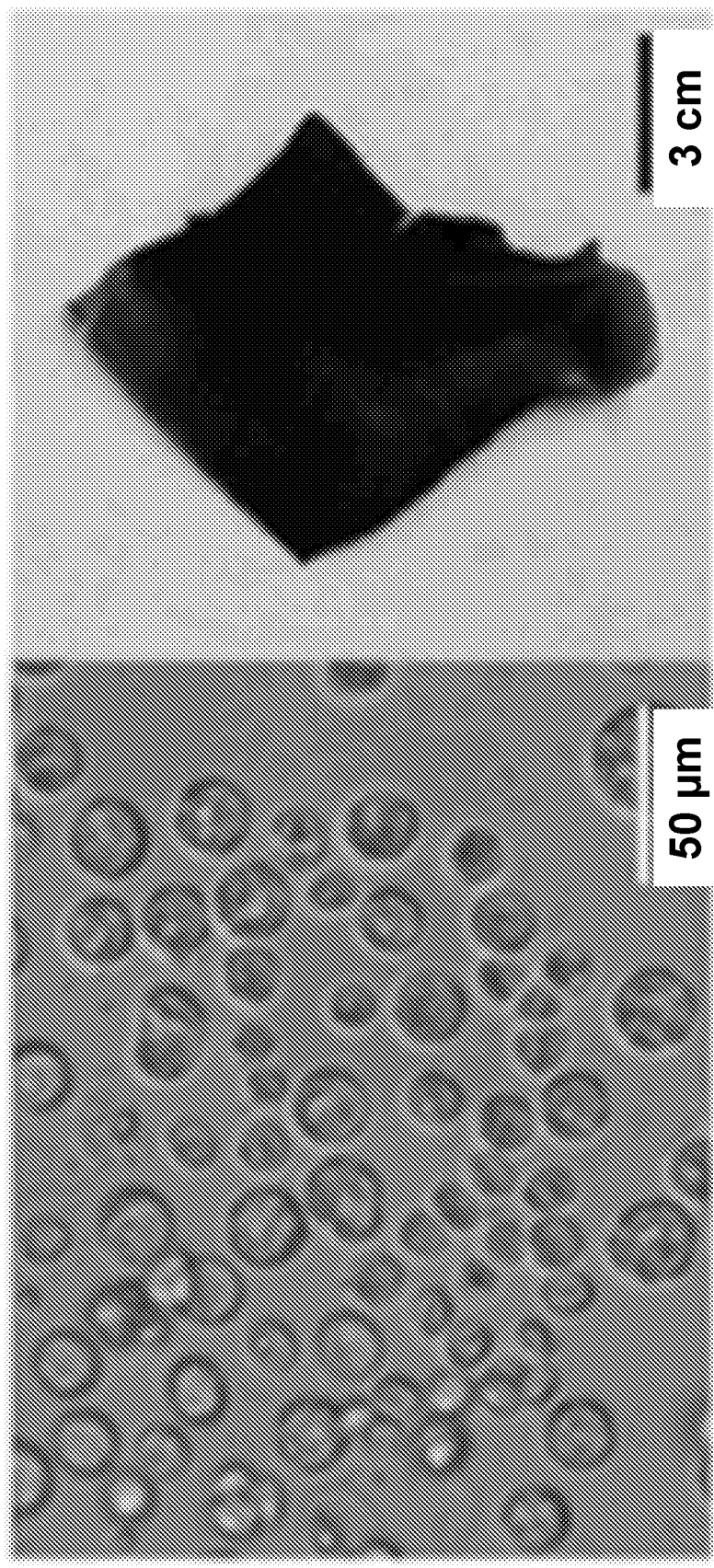
FIGS. 12A-B illustrate an embodiment of a cultured microalgae turned into algaplastics.

A method that turns microalgal cultures into bioplastics is disclosed. The method includes 1) a selection of microalgal strains, 2) a procedure to make the microalgae convert the cellular components into bioplastic materials (algaplastics), and 3) a chemical reaction to alternate the physical character of the algaplastics. Microalgal strains that are suitable for algaplastic production were identified. FIG. 12A shows the microalga *Chlorella vulgaris* grown in the lab. FIG. 12B shows algaplastic film made from *Chlorella vulgaris* after converting the cellular components into algaplastics.

Microalgae, *Chlorella vulgaris* and *Chlamydomonas reinhardtii*, were cultured in water containing nutrients necessary for their growth (FIG. 12A). A stationary phase of the cultured microalgae was harvested by centrifugation. The precipitate was then agitated overnight to convert the cellular components into algaplastics that are composed of starch, triglyceride, cellulose, proteins, and other biomaterials. The algaplastics can be stored as a film after dehydration until they are used for molding (FIG. 12B). To mold the algaplastics, the algaplastics were first ground into a fine powder, then mixed into water. The mixture was heated to 120° C. for molding.

Aspects of the Invention

Various aspects of the present disclosure are described below in the following clauses.

Clause 1. A bioplastic mass comprising triacylglycerol-accumulated *Chlamydomonas*.

Clause 2. The bioplastic mass of clause 1, wherein the triacylglycerol-accumulated *Chlamydomonas* is cross-linked.

Clause 3, The bioplastic mass of clause 2, further comprising *Chlorella*, wherein the triacylglycerol-accumulated *Chlamydomonas* is crosslinked with *Chlorella*.

Clause 4. The bioplastic mass of any one of the preceding clauses, wherein the crosslinking is performed under heated conditions of about 120° C.

Clause 5. The bioplastic mass of any one of the preceding clauses, further comprising an additive.

Clause 6. The bioplastic mass of clause 5, wherein the additive is selected from ammonium persulfate, hydrogen peroxide, sodium persulfate, polyethylene, glycerol, and a combination thereof.

Clause 7. The bioplastic mass of any one of the preceding clauses, wherein the triacylglycerol-accumulated *Chlamydomonas* is produced by centrifugation.

Clause 8. A method for making bioplastics comprising:
culturing one or more genus of microalgae, wherein at least one of the genera is a triacylglycerol-accumulating microalgae;
centrifuging the microalgae during the stationary phase to induce polymer compound accumulation;
extracting compounds from precipitate formed during centrifugation;
incubating and dehydrating the precipitate;
grinding the precipitate to form a powder and mixing with water to form a mixture; and
adding at least one additive to form the bioplastic, wherein the additive is selected from an oxidizer, a plasticizer, and a combination thereof.

Clause 9. The method of clause 8, wherein the microalgae comprises *Chlamydomonas*.

Clause 10. The method of clause 9, wherein the microalgae further comprises *Chlorella*.

Clause 11. The method of clause 10, wherein triacylglycerol-accumulating microalgae is *Chlamydomonas reinhardtii*, and the *Chlorella* is *Chlorella vulgaris*;

and wherein the accumulated polymer produced by *Chlorella vulgaris* is selected from starch, triglyceride, cellulose, proteins, and a combination thereof.

Clause 12. The method of clause 8, wherein the additive is selected from ammonium persulfate, hydrogen peroxide, sodium persulfate, polyethylene, glycerol, and a combination thereof.

Clause 13. The method of clause 8, wherein the additive is from about 5% w/dw to about 15% w/dw of the biomass.

Clause 14. The method of clause 8, wherein the method further comprises eluting carotenoids from supernatant generated during the centrifugation.

Clause 15. A method for making bioplastics comprising:
culturing one or more genus of microalgae, wherein at least one of the genera is a triacylglycerol-accumulating microalgae;
centrifuging the microalgae during the stationary phase to induce polymer compound accumulation;
extracting precipitate formed during centrifugation;
incubating and dehydrating the precipitate;
grinding the precipitate to form a powder and mixing with water to form a mixture;
adding at least one additive to the mixture to form the bioplastic.
wherein the additive is selected from an oxidizer, a plasticizer, and a combination thereof;
heating the mixture to about 120° C.; and
molding the mixture into a shape.

Clause 16. The method of clause 15, wherein the microalgae comprises *Chlamydomonas* and optionally includes *Chlorella*.

Clause 17. The method of clause 16, wherein when the microalgae comprises *Chlamydomonas reinhardtii*, and optionally includes *Chlorella vulgaris*;
wherein the accumulated polymer from *Chlamydomonas reinhardtii* is triacylglycerol, and
wherein the accumulated polymer from *Chlorella vulgaris* is selected from starch, triglyceride, cellulose, proteins, and a combination thereof.

Clause 18. The method of clause 15, wherein the additive is selected from ammonium persulfate, hydrogen peroxide, sodium persulfate, polyethylene, glycerol, and a combination thereof.

Clause 19. The method of clause 15, wherein the additive is from about 5% w/dw to about 15% w/dw of the biomass.

Clause 20. The method of clause 15, wherein the method further comprises eluting carotenoids from supernatant generated during the centrifugation.

Clause 21. A bioplastic mass formed by the steps of:
culturing one or more genus of microalgae, wherein at least one of the genera is a triacylglycerol-accumulating microalgae;
centrifuging the microalgae during the stationary phase to induce polymer compound accumulation;
extracting compounds from precipitate formed during centrifugation;
incubating and dehydrating the precipitate;
grinding the precipitate to form a powder and mixing with water to form a mixture; and
adding at least one additive to form the bioplastic, wherein the additive is selected from an oxidizer, a plasticizer, and a combination thereof.

Clause 22. The bioplastic mass of clause 21, further formed by the additional steps of:
heating the mixture to about 120° C.; and
molding the mixture into a shape.

Clause 23. The bioplastic mass of clauses 21 or 22, wherein the microalgae comprises *Chlamydomonas* and optionally includes *Chlorella*.

Clause 24. The bioplastic mass of clauses 23, wherein when the microalgae comprises *Chlamydomonas reinhardtii* and *Chlorella vulgaris*:
wherein the accumulated polymer from *Chlamydomonas reinhardtii* is triacylglycerol; and wherein the accumulated polymer from *Chlorella vulgaris* is selected from starch; triglyceride, cellulose, proteins, and a combination thereof.

Clause 25. The bioplastic mass of any one of clauses 21-24, wherein the additive is selected from ammonium persulfate, hydrogen peroxide, sodium persulfate, polyethylene, glycerol, and a combination thereof.

Clause 26. The bioplastic mass of any one of clauses 21-25, wherein the additive is from about 5% w/dw to about 15% w/dw of the biomass.

Clause 27. The bioplastic mass of any one of claims 21-25, wherein the extracted compound comprises carotenoids.

Clause 28. An alga mixed plastic comprising triacylglycerol-accumulated microalgae and polyethylene.

Clause 29. The alga mixed plastic of clause 28, wherein the triacylglycerol-accumulated microalgae is *Chlamydomonas*.

Clause 30, The alga mixed plastic of any one of the preceding clauses, further comprising *Chlorella*.

Clause 31. The alga mixed plastic of any one of the preceding clauses, further comprising an additive selected from ammonium persulfate, glycerol, and a combination thereof.

Clause 32. The alga mixed plastic of any one of the preceding clauses, wherein the triacylglycerol-accumulated *Chlamydomonas* is produced by centrifugation.

Clause 33. A method of producing triacylglycerol-accumulated microalgae, comprising:
selecting and culturing a species of microalgae capable of triacylglycerol accumulation from centrifugation;
centrifuging the cultured microalgae during the stationary phase of growth;
extracting precipitate formed during centrifugation;
incubating the precipitate, resulting in triacylglycerol-accumulated microalgae.

Clause 34. The method of clause 33, wherein the cultured species of microalgae is from the genus *Chlamydomonas*.

Clause 35. The triacylglycerol-accumulated microalgae of clause 33, wherein the amount of triacylglycerol accumulated in the microalgae after incubation is from about 200% to about 400% higher than triacylglycerol accumulation produced by microalgae subjected to stress conditions other than centrifugation.

Clause 36. The triacylglycerol-accumulated microalgae of clause 33, wherein the microalgae contains less C18 fatty acid methyl esters than in a comparable sample produced by nitrogen depletion.

Clause 37. Alga mixed plastic beads formed by the process of:
culturing one or more genus of microalgae, wherein at least one of the genera is a triacylglycerol-accumulating microalgae;
centrifuging the microalgae during the stationary phase to induce polymer compound accumulation;

extracting precipitate formed during centrifugation;
incubating and dehydrating the precipitate;
grinding the precipitate to form a powder and mixing with water to form a mixture;
adding at least one additive to the mixture to form the bioplastic.
wherein the additive is selected from an oxidizer, a plasticizer, and a combination thereof;
heating the mixture to about 120° C.; and
molding the mixture into a shape.

Clause 38. The alga mixed plastic beads of claim 37, wherein the microalgae comprises *Chlamydomonas* and optionally includes *Chlorella*.

Clause 39. The alga mixed plastic beads of any one of the preceding clauses, wherein the accumulated polymer from *Chlamydomonas reinhardtii* is triacylglycerol; and
wherein the accumulated polymer from *Chlorella vulgaris* is selected from starch, triglyceride, cellulose, proteins, and a combination thereof.

Clause 40. The alga mixed plastic beads of any one of the preceding clauses; wherein the additive is selected from ammonium persulfate, hydrogen peroxide, sodium persulfate, polyethylene, glycerol, and a combination thereof.

Clause 41. The alga mixed plastic beads of any one of the preceding clauses, wherein the additive is from about 5% w/dw to about 15% w/dw of the biomass.

Clause 42. A thermoplastic including the bioplastic mass of any one of clauses 21-27.

REFERENCES

[6] V. Ivanov, V. Stabnikov, Z. Ahmed, S. Dobrenko, A. Saliuk, Production and applications of crude polyhydroxyalkanoate-containing bioplastic from the organic fraction of municipal solid waste, International Journal of Environmental Science and Technology, 12 (2015) 725-738.

[7] F. Seniha Güner, Y. Yağci, A. Tuncer Erciyes, Polymers from triglyceride oils, Progress in Polymer Science; 31 (2006) 633-670.

[8] M. Galiá, L. M. de Espinosa, J. C. Ronda, G. Lligadas, V. Cádiz, Vegetable oil-based thermosetting polymers; European Journal of Lipid Science and Technology; 112 (2010) 87-96.

[9] Y. Ghasemi, S. Rasoul-Amini, A. T. Naseri, N. Montazeri-Najafabady, M. A. Mobasher, F. Dabbagh, Microalgae biofuel potentials (review); Prikl Biokhim Mikrobiol, 48 (2012) 150-168.

[10] E. H. Harris, *Chlamydomonas* as a Model Organism, Annu. Rev. Plant Physiol. Plant Molec. Biol., 52 (2001) 363-406.

[11] M. Siaut, S. Cuine, C. Cagnon, B. Fessler, M. Nguyen, P. Carrier, A. Beyly, F. Beisson, C. Triantaphylides, Y. Li-Beisson, G. Peltier, Oil accumulation in the model green alga *Chlamydomonas reinhardtii*: characterization, variability between common laboratory strains and relationship with starch reserves, BMC biotechnology, 11 (2011) 7.

[12] E. I. Urzica, A. Vieler; A. Hong-Hermesdort M. D. Page, D. Casero, S. D. Gallaher, J. Kropat, M. Pellegrini, C. Benning, S. S. Merchant, Remodeling of membrane lipids in iron-starved *Chlamydomonas*, J Biol Chem, 288 (2013) 30246-30258.

[13] B. Legeret, M. Schulz-Raffelt, H. M. Nguyen, P. Auroy, F. Beisson, G. Peltier, G. Blanc, Y. Li-Beisson, Lipidomic and transcriptomic analyses of *Chlamydomonas reinhardtii* under heat stress unveil a direct route for the conversion of membrane lipids into storage lipids, Plant Cell Environ, 39 (2016) 834-847.

[14] N. Kato, T. Dong, M. Bailey, T. Lum, D. Ingram, Triacylglycerol mobilization is suppressed by brefeldin A in *Chlamydomonas reinhardtii*, Plant & cell physiology, 54 (2013) 1585-1599.

[15] D. S. Gorman, R. P. Levine, Cytochrome f and plastocyanin: their sequence in the photosynthetic electron transport chain of *Chlamydomonas reinhardi*, Proc Natl Acad Sci USA, 54 (1965) 1665-1669.

[16] H. C. Bold; The Morphology of *Chlamydomonas chlamydogama*, Sp. Nov, Bulletin of the Torrey Botanical Club, 76 (1949) 101-108.

[17] K. Mikami, M. Hosokawa, Biosynthetic pathway and health benefits of fucoxanthin, an algae-specific xanthophyll in brown seaweeds, Int J Mol Sci, 14 (2013) 13763-13781.

[18] E. C. Goncalves, A. C. Wilkie, M. Kirst, B. Rathinasabapathi; Metabolic regulation of triacylglycerol accumulation in the green algae: identification of potential targets for engineering to improve oil yield, Plant Biotechnol J, 14 (2016) 1649-1660.

[19] M. Iwai, K. Ikeda, M. Shimojima, H. Ohta, Enhancement of extraplastidic oil synthesis in *Chlamydomonas reinhardtii* using a type-2 diacylglycerol acyltransferase with a phosphorus starvation-inducible promoter; Plant Biotechnol J, 12 (2014) 808-819.

[20] H. Vigeolas, J. T. van Dongen, P. Waldeck, D. Hühn, P. Geigenberger, Lipid Storage Metabolism Is Limited by the Prevailing Low Oxygen Concentrations within Developing Seeds of Oilseed Rape, Plant Physiology, 133 (2003) 2048.

[21] T. Ide, S. Mochiji, N. Ueki; K. Yamaguchi, S. Shigenobu, M. Hirono, K.-i. Wakabayashi; Identification of the agg1 mutation responsible for negative phototaxis in a "wild-type" strain of *Chlamydomonas reinhardtii*, Biochemistry and Biophysics Reports, 7 (2016) 379-385.

[22] I. Branyikova, B. Marsalkova, J. Doucha, T. Branyik, K. Bisova, V. Zachleder, M. Vitova, Microalgae—novel highly efficient starch producers, Biotechnol Bioeng, 108 (2011) 766-776.

[23] R. Praveenkumar, B. Kim; J. Lee, D. Vijayan, K. Lee, B. Nam, S. G. Jeon, D. M. Kim, Y. K. Oh, Mild pressure induces rapid accumulation of neutral lipid (triacylglycerol) in *Chlorella* spp, Bioresour Technol, 220 (2016) 661-665.

[24] S. K. Min, G. H. Yoon, J. H. Joo, S. J. Sim, H. S. Shin, Mechanosensitive physiology of *Chlamydomonas reinhardtii* under direct membrane distortion, Sci Rep, 4 (2014) 4675.

[25] S. Rabbani, P. Beyer, J. Lintig, P, Hugueney, H. Kleinig, Induced beta-carotene synthesis driven by triacylglycerol deposition in the unicellular alga *Dunaliella bardawil*, Plant Physiol, 116 (1998) 1239-1248,

[26] I. Couso, M. Vila, J. Vigara, B. F. Cordero, M. Ä. Vargas, H. Rodrïguez, R. León, Synthesis of carotenoids and regulation of the carotenoid biosynthesis pathway in response to high light stress in the unicellular microalga *Chlamydomonas reinhardtii*, European Journal of Phycology, 47 (2012) 223-232,

[27] J. Mares, Lutein and Zeaxanthin Isomers in Eye Health and Disease, Annual Review of Nutrition, 36 (2016) 571-602.

[28] C. Goodson, R. Roth, Z. T. Wang, U. Goodenough, Structural correlates of cytoplasmic and chloroplast lipid body synthesis in *Chlamydomonas reinhardtii* and stimulation of lipid body production with acetate boost, Eukaryot Cell, 10 (2011) 1592-1606.
[29] K. Sakurai, T. Moriyama, N. Sato, Detailed identification of fatty acid isomers sheds light on the probable precursors of triacylglycerol accumulation in photoautotrophically grown *Chlamydomonas reinhardtii*, Eukaryot Cell, 13 (2014) 256-266.
[30] N. Kobayashi, E. A. Noel, A. Barnes, J. Rosenberg, C. DiRusso, P. Black, G. A. Oyler, Rapid detection and quantification of triacylglycerol by HPLC-ELSD in *Chlamydomonas reinhardtii* and *Chlorella* strains, Lipids, 48 (2013) 1035-1049.
[31] J. Fan, C. Andre, C. Ku, A chloroplast pathway for the de novo biosynthesis of triacylglycerol in *Chlamydomonas reinhardtii*, FEBS Lett, 585 (2011) 1985-1991,
[32] B. V. Venkatarama Reddy, A. Gupta, Strength and Elastic Properties of Stabilized Mud Block Masonry Using Cement-Soil Mortars, Journal of Materials in Civil Engineering, 18 (2006) 472-476.
[33] C. Y. Chen, Jesisca, C. Hsieh, D. J. Lee, C. H. Chang, J. S. Chang, Production, extraction and stabilization of lutein from microalga *Chlorella sorokiniana* MB-1, Bioresour Technol, 200 (2016) 500-505.
[34] Rajendran et al., 2012. Seaweeds can be a new source for bioplastics. J. Pharm. Res. 5(3), 1476-1479.
[35] Becker 2007. Micro-algae as a source of protein. Biotechnol. Adv. 25, 207-210.
[36] Wang et al., 2016. Modification of Protein Rich Algal-Biomass to Form Bioplastics and Odor Removal.
[37] Scaife, M. et al., 2015. Establishing *Chlamydomonas reinhardtii* as an industrial biotechnology host. The Plant Journal (2015) 82, 532-546.
[38] Zeller, M. A., Hunt, R., Jones, A. and Sharma, S. (2013), Bioplastics and their thermoplastic blends from *Spirulina* and *Chlorella* microalgae. J. Appl. Polym. Sci., 130: 3263-3275.
[39] S. Puhan, N. Saravanan, G. Nagarajan, N. Vedaraman, Effect of biodiesel unsaturated fatty acid on combustion characteristics of a DI compression ignition engine, Biomass and Bioenergy, 34 (2010) 1079-1088.
[40] R. Micha, D. Mozaffarian, Saturated fat and cardiometabolic risk factors, coronary heart disease, stroke, and diabetes: a fresh look at the evidence, Lipids, 45 (2010) 893-905.
[41] M. L. Hamilton, J. Warwick, A. Terry, M. J. Allen, J. A. Napier, O. Sayanova, Towards the Industrial Production of Omega-3 Long Chain Polyunsaturated Fatty Acids from a Genetically Modified Diatom *Phaeodactylum tricornutum*, PLoS One, 10 (2015) e0144054.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, "about 0" can refer to 0, 0.001, 0.01, or 0.1. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

I claim at least the following:

1. A bioplastic mass comprising triacylglycerol-accumulated *Chlamydomonas* and an additive;
    wherein the additive is selected from an oxidizer, a plasticizer, and a combination thereof; and
    wherein the triacylglycerol is accumulated by centrifugation of *Chlamydomonas* during a stationary phase of culturing.

2. The bioplastic mass of claim 1, wherein the triacylglycerol-accumulated *Chlamydomonas* is crosslinked.

3. The bioplastic mass of claim 2, further comprising *Chlorella*, wherein the triacylglycerol-accumulated *Chlamydomonas* is crosslinked with *Chlorella*.

4. The bioplastic mass of claim 1, wherein the additive is selected from the group consisting of ammonium persulfate, hydrogen peroxide, sodium persulfate, polyethylene, glycerol, and a combination thereof.

5. The bioplastic mass of claim 1, wherein the triacylglycerol-accumulated *Chlamydomonas* is produced by centrifugation of *Chlamydomonas reinhardtii*.

6. The bioplastic mass of claim 1, wherein the triacylglycerol-accumulated *Chlamydomonas* comprises about 38 to 72 µg of triacylglycerol per $10^6$ cells.

7. The bioplastic mass of claim 1, wherein the triacylglycerol-accumulated *Chlamydomonas* comprises about 1% (mol/mol) or less of unsaturated C18 fatty acids in a total amount of the triacylglycerol.

8. A bioplastic mass comprising triacylglycerol-accumulated *Chlamydomonas*, wherein the triacylglycerol-accumulated *Chlamydomonas* comprises about 38 to 72 µg of triacylglycerol per $10^6$ cells and about 1% (mol/mol) or less of unsaturated C18 fatty acids in a total amount of the triacylglycerol.

9. The bioplastic mass according to claim 8, wherein the amount of triacylglycerol accumulated in the *Chlamydomonas* after incubation is from about 200% to about 400% higher than triacylglycerol accumulation produced by microalgae subjected to stress conditions other than centrifugation and a lower percentage of C18 fatty acid methyl esters than in a comparable triacylglycerol-accumulated microalgae produced by nitrogen depletion.

10. The bioplastic mass according to claim 8, wherein the accumulated triacylglycerol triacylglycerol-accumulated *Chlamydomonas* is crosslinked with *Chlorella* at about 120° C., and wherein the bioplastic mass further comprises an additive,
    wherein the additive comprises about 5% by weight relative to dry weight of the bioplastic mass (w/dw) to about 15% w/dw of the bioplastic mass, and wherein the additive is selected from ammonium persulfate, hydrogen peroxide, sodium persulfate, polyethylene, glycerol, and a combination thereof.

* * * * *